United States Patent
Lin et al.

(10) Patent No.: US 10,801,031 B2
(45) Date of Patent: Oct. 13, 2020

(54) SHUTTLE VECTOR, PROKARYOTIC HOST CELLS, KIT, AND METHOD FOR PRODUCING PROTEINS

(71) Applicant: Agricultural Technology Research Institute, Hsinchu (TW)

(72) Inventors: Jiunn-Horng Lin, Hsinchu (TW);
Jyh-Perng Wang, Hsinchu (TW);
Zeng-Weng Chen, Hsinchu (TW);
Wen-Zheng Huang, Hsinchu (TW);
Hung-Chih Wang, Hsinchu (TW);
Shih-Ling Hsuan, Hsinchu (TW)

(73) Assignee: AGRICULTURAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 16/136,902

(22) Filed: Sep. 20, 2018

(65) Prior Publication Data
US 2019/0093113 A1    Mar. 28, 2019

(30) Foreign Application Priority Data
Sep. 27, 2017  (TW) .............................. 106133120 A

(51) Int. Cl.
*C12N 15/74* (2006.01)
*C12N 15/75* (2006.01)
*C12N 15/70* (2006.01)

(52) U.S. Cl.
CPC .......... *C12N 15/746* (2013.01); *C12N 15/70* (2013.01); *C12N 15/74* (2013.01); *C12N 15/75* (2013.01); *C12N 2800/101* (2013.01); *C12N 2800/204* (2013.01)

(58) Field of Classification Search
None
See application file for complete search history.

(56) References Cited

FOREIGN PATENT DOCUMENTS

| EP | 1 493 808 A1 | 1/2005 |
| JP | 2003235565 A | * 8/2003 |
| TW | I565799 B | 1/2017 |

OTHER PUBLICATIONS

Chen et al., "Construction and Applicaton of a New *Escherichia coli*/ Lactobacillus Shuttle Vector". Taiwanese Journal of Agricultural Chemistry and Food Science (Oct. 2016) vol. 54 No. 5: 236-246.
Eom et al., "Construction of theta-type shuttle vector from Leuconostoc and other lactic acid bacteria usng pCB42 isolated from kimchi". Plasmid vol. 67 (2012) 35-43.
Fang et al., "Sequencing and Characterization of a Cryptic Plasmid pLP-8 from *Lactobacillus plantarum*". Taiwanese Journal of Agricultural Chemistry and Food Science (Jun. 2015) vol. 53 No. 3: 81-89.
Leer et al., "Structural and functional analysis of two cryptic plasmids from *Lactobacillus pentosus* MD353 and *Lactobacillus plantarum* ATCC 8014". Mol Gen Genet (1992) vol. 234:265-274.
Xi et al., "Characterization of three cryptic plasmids from *Lactobacillus plantarum* G63 that was isolated from Chinese pickle". Plasmid vol. 70 (2013) 321-328.

* cited by examiner

*Primary Examiner* — Mindy G Brown
*Assistant Examiner* — Tiffany Nicole Grooms
(74) *Attorney, Agent, or Firm* — Birch, Stewart, Kolasch & Birch, LLP

(57) ABSTRACT

A shuttle vector is provided which can be manipulated in various kinds of host cells, thereby providing a novel tool for the field of genetic engineering. Also provided are a prokaryotic host cell and a kit including said shuttle vector, so as to construct expression vectors which contain the target gene using the shuttle vector, thereby producing proteins in various host cells with one single vector.

22 Claims, 4 Drawing Sheets

Specification includes a Sequence Listing.

SEQUENCE LISTING

<160> NUMBER OF SEQ ID NOS: 25

<210> SEQ ID NO 1
<211> LENGTH: 1753
<212> TYPE: DNA
<213> ORGANISM: Artificial Sequence
<220> FEATURE:
<223> OTHER INFORMATION: Complete sequence of pLP31-8

<400> SEQUENCE: 1

| | | | | | |
|---|---|---|---|---|---|
| tttaaaaata | gcaatgaaaa | aatccgaaga | aaatgtcaaa | ggtacactta | cacgtcatca | 60 |
| aagatgacgc | tgtgctaaac | ccattaaaac | ctgtatcaga | tttcgctttg | ctcaaacaaa | 120 |
| actgacttgc | gtcagttgga | atctttaaag | ccaataaagt | ccagtcgcca | actccttcgg | 180 |
| actttattgg | ctttaaagat | tggctttaaa | tgcccctaat | ttgctctcta | agccatttta | 240 |
| gctgttaacc | gtataattta | ctgtccgtca | acggtaaatc | gacgtagaac | ggcttttagc | 300 |
| cgttctagga | ggctttaagg | agttgacaga | ctcactagac | caagacactt | ttgcgcatgc | 360 |
| aaagaaaagc | acacctgctt | tttttgcctg | cctcacggcg | agtgcagggt | gagtttgagc | 420 |
| gggagctccc | gctcatttat | ggggtcaagc | tgacacagct | tgcgggtttg | ggcagcgccc | 480 |
| atggttttat | tcgtgtggga | tagaaatttg | aaaatcaggg | ggggcgaggg | agcgaatttt | 540 |
| gcgaccgtac | tacgaccccc | cctttaagtg | ccgagtgcca | aaactgaatt | ttaggtggct | 600 |
| tcaggtctac | tctcccaagg | gattagtcca | ctttattatt | gagcgacatt | ttggcgacat | 660 |
| tttggtgatt | tttttgaatt | taatacgtat | tttgttgcat | taaatacgta | attatgctac | 720 |
| tttttcttta | gtgaatattt | gaaggaggtt | agaaattttg | gaaagtaaaa | agagattgac | 780 |
| gattacgtta | tcgagtcaag | ttcttgaata | tttgtcggag | actgcgaaaa | acaaaggttt | 840 |
| atctaaatct | gcattgatta | cagttgcact | agaaaaatac | aaggaagggc | agaaatgagc | 900 |
| acaaaaaaag | agcgtacccg | ctgaaaagtt | cgctcgattg | ttgcttattc | tgataaggcg | 960 |
| attttaacat | tatggctaaa | gacaaggcaa | ggtacttcac | ttttttgcta | tatccggaaa | 1020 |
| gtattccaaa | tgattggaat | caacgcttgg | aactgatggg | cgttcctatt | gcgattagtc | 1080 |
| ctctgcatga | tagggataag | agcaatgttg | aagggcagac | gtacaagaaa | gctcattatc | 1140 |
| atgttgttta | tgtggcaaaa | aatcctgtta | cgacggatag | cgttaggaaa | agaatccaaa | 1200 |
| gggctttggg | gcctagaagc | gtttctaaag | tgcaaattgt | tgctcagagc | atgaaaaata | 1260 |
| tgtatttgta | tctgacacat | gaatctaaag | acgctattgc | taaaaataag | cacaagtaca | 1320 |
| gcaagcacga | cattactttg | ctgaacaatt | ttgatattga | tcgctatatt | acgcttgatg | 1380 |
| ttgaagacaa | agacgacatg | ctgaatgatg | tttgtgattt | gattgatgac | cataatttgg | 1440 |
| caaatatgcg | tgaactgaga | cgcttttaa | aagctcatgt | tcagaatat | ggcatacccg | 1500 |
| gtattaaagt | cgtcaattcg | gttttacgtg | ctcatactgg | actgataagg | ctgtatttcg | 1560 |
| atgctgttta | tcaggaacgc | aagtacggca | gaggcgatat | aaacaaagag | accggtgaga | 1620 |
| tacaagacta | attagcaaat | gaaaattggg | tgctcaattg | agcgcctttt | ttgttgtcgg | 1680 |
| ctagccgact | tctgatacag | gtttaagtgt | tttagcacaa | ctccaattta | tttggagtgt | 1740 |
| aagtgcgcat | tgc | | | | | 1753 |

<210> SEQ ID NO 2
<211> LENGTH: 4099
<212> TYPE: DNA
<213> ORGANISM: Artificial Sequence
<220> FEATURE:
<223> OTHER INFORMATION: Complete sequence of pBRLP31-8

<400> SEQUENCE: 2

```
ggtaccaaag catgcaatga gctcagtaac ccgtatcgtg agcatcctct ctcgtttcat      60
cggtatcatt accccatga acagaaatcc cccttacacg gaggcatcag tgaccaaaca     120
ggaaaaaacc gcccttaaca tggcccgctt tatcagaagc cagacattaa cgcttctgga     180
gaaactcaac gagctggacg cggatgaaca ggcagacatc tgtgaatcgc ttcacgacca     240
cgctgatgag ctttaccgca gctgcctcgc gcgtttcggt gatgacggtg aaaacctctg     300
acacatgcag ctcccggaga cggtcacagc ttgtctgtaa gcggatgccg ggagcagaca     360
agcccgtcag ggcgcgtcag cgggtgttgg cgggtgtcgg ggcgcagcca tgacccagtc     420
acgtagcgat agcggagtgt atactggctt aactatgcgg catcagagca gattgtactg     480
agagtgcacc attgcggtgt gaaataccgc acagatgcgt aaggagaaaa taccgcatca     540
ggcgctcttc cgcttcctcg ctcactgact cgctgcgctc ggtcgttcgg ctgcggcgag     600
cggtatcagc tcactcaaag gcggtaatac ggttatccac agaatcaggg gataacgcag     660
gaaagaacat gtgagcaaaa ggccagcaaa aggccaggaa ccgtaaaaag gccgcgttgc     720
tggcgttttt ccataggctc cgcccccctg acgagcatca caaaaatcga cgctcaagtc     780
agaggtggcg aaacccgaca ggactataaa gataccaggc gtttccccct ggaagctccc     840
tcgtgcgctc tcctgttccg accctgccgc ttaccggata cctgtccgcc tttctccctt     900
cgggaagcgt ggcgctttct catagctcac gctgtaggta tctcagttcg gtgtaggtcg     960
ttcgctccaa gctgggctgt gtgcacgaac cccccgttca gcccgaccgc tgcgccttat    1020
ccggtaacta tcgtcttgag tccaacccgg taagacacga cttatcgcca ctggcagcag    1080
ccactggtaa caggattagc agagcgaggt atgtaggcgg tgctacagag ttcttgaagt    1140
ggtggcctaa ctacggctac actagaagga cagtatttgg tatctgcgct ctgctgaagc    1200
cagttacctt cggaaaaaga gttggtagct cttgatccgg caaacaaacc accgctggta    1260
gcggtggttt ttttgtttgc aagcagcaga ttacgcgcag aaaaaaagga tctcaagaag    1320
atcctttgat cttttctacg gggtctgacg ctcagtggaa cgaaaactca cgttaaggga    1380
ttttggtcat gaacaataaa actgtctgct tacataaaca gtaatacaag gggtgttatg    1440
agccatatca acgggaaacg ctcgagtacg tatctagagc aaagcttatc gtcgacatgc    1500
atctgcagcc ggggggatcc tcgcgacata tgactagtga attcgcaatg cgcacttaca    1560
ctccaaataa attggagttg tgctaaaaca cttaaacctg tatcagaagt cggctagccg    1620
acaacaaaaa aggcgctcaa ttgagcaccc aattttcatt tgctaattag tcttgtatct    1680
caccggtctc tttgtttata tcgcctctgc cgtacttgcg ttcctgataa acagcatcga    1740
aatacagcct tatcagtcca gtatgagcac gtaaaccgaa ttgacgact ttaataccgg     1800
gtatgccata ttctgaacca tgagctttta aaaagcgtct cagttcacgc atatttgcca    1860
aattatggtc atcaatcaaa tcacaaacat cattcagcat gtcgtctttg tcttcaacat    1920
caagcgtaat atagcgatca atatcaaaat tgttcagcaa agtaatgtcg tgcttgctgt    1980
acttgtgctt atttttagca atagcgtctt tagattcatg tgtcagatac aaatacatat    2040
ttttcatgct ctgagcaaca atttgcactt tagaaacgct tctaggcccc aaagcccttt    2100
ggattctttt cctaacgcta tccgtcgtaa caggatttt tgccacataa acaacatgat     2160
aatgagcttt cttgtacgtc tgcccttcaa cattgctctt atccctatca tgcagaggac    2220
taatcgcaat aggaacgccc atcagttcca agcgttgatt ccaatcattt ggaatacttt    2280
```

```
ccggatatag caaaaaagtg aagtaccttg ccttgtcttt agccataatg ttaaaatcgc    2340
cttatcagaa taagcaacaa tcgagcgaac ttttcagcgg gtacgctctt tttttgtgct    2400
catttctgcc cttccttgta ttttctagt gcaactgtaa tcaatgcaga tttagataaa     2460
cctttgtttt tcgcagtctc cgacaaatat tcaagaactt gactcgataa cgtaatcgtc    2520
aatctctttt tactttccaa aatttctaac ctccttcaaa tattcactaa agaaaaagta    2580
gcataattac gtatttaatg caacaaaata cgtattaaat tcaaaaaaat caccaaaatg    2640
tcgccaaaat gtcgctcaat aataaagtgg actaatccct tgggagagta gacctgaagc    2700
cacctaaaat tcagttttgg cactcggcac ttaaggggg gtcgtagta cggtcgcaaa      2760 attcgctccc tcgcccccccc tgattttcaa atttctatcc cacacgaata aaaccatggg    2820
cgctgcccaa acccgcaagc tgtgtcagct tgaccccata aatgagcggg agctcccgct    2880
caaactcacc ctgcactcgc cgtgaggcag gcaaaaaaag caggtgtgct tttctttgca    2940
tgcgcaaaag tgtcttggtc tagtgagtct gtcaactcct taaagcctcc tagaacggct    3000
aaaagccgtt ctacgtcgat ttaccgttga cggacagtaa attatacggt taacagctaa    3060
aatggcttag agagcaaatt aggggcattt aaagccaatc tttaaagcca ataaagtccg     3120
aaggagttgg cgactggact ttattggctt taaagattcc aactgacgca agtcagtttt    3180
gtttgagcaa agcgaaatct gatacagttt taatgggttt agcacagcgt catctttgat    3240
gacgtgtaag tgtacctttg acattttctt cggatttttt cattgctatt tttaaaagat    3300
cttagtgaca ttagaaaacc gactgtaaaa agtacagtcg gcattatctc atattataaa    3360
agccagtcat taggcctatc tgacaattcc tgaatagagt tcataaacaa tcctgcatga    3420
taaccatcac aaacagaatg atgtacctgt aaagatagcg gtaaatatat tgaattacct    3480
ttattaatga attttcctgc tgtaataatg ggtagaaggt aattactatt attattgata    3540
tttaagttaa acccagtaaa tgaagtccat ggaataatag aaagagaaaa agcattttca    3600
ggtataggtg ttttgggaaa caatttcccc gaaccattat attctctac atcagaaagg     3660 tataaatcat aaaactcttt gaagtcattc tttacaggag tccaaatacc agagaatgtt    3720
ttagatacac catcaaaaat tgtataaagt ggctctaact tatcccaata acctaactct    3780
ccgtcgctat tgtaaccagt tctaaaagct gtatttgagt ttatcaccct tgtcactaag    3840
aaaataaatg cagggtaaaa tttatatcct tcttgttta tgtttcggta taaaacacta     3900
atatcaattt ctgtggttat actaaaagtc gtttgttggt tcaaataatg attaaatatc    3960
tcttttctct tccaattgtc taaatcaatt ttattaaagt tcatttgata tgcctcctaa    4020
atttttatct aaagtgaatt taggaggctt acttgtctgc tttcttcatt agaatcaatc    4080
cttttttaaa agtcaatcc                                                 4099
```

<210> SEQ ID NO 3
<211> LENGTH: 617
<212> TYPE: DNA
<213> ORGANISM: Artificial Sequence
<220> FEATURE:
<223> OTHER INFORMATION: E. coli plasmid replicon

<400> SEQUENCE: 3

```
gcgttgctgg cgttttttcca taggctccgc cccctgacg agcatcacaa aaatcgacgc      60
tcaagtcaga ggtggcgaaa cccgacagga ctataaagat accaggcgtt tcccctgga     120 agctccctcg tgcgctctcc tgttccgacc ctgccgctta ccggatacct gtccgccttt    180
ctcccttcgg gaagcgtggc gctttctcat agctcacgct gtaggtatct cagttcggtg    240
```

```
taggtcgttc gctccaagct gggctgtgtg cacgaacccc ccgttcagcc cgaccgctgc    300
gccttatccg gtaactatcg tcttgagtcc aacccggtaa gacacgactt atcgccactg    360
gcagcagcca ctggtaacag gattagcaga gcgaggtatg taggcggtgc tacagagttc    420
ttgaagtggt ggcctaacta cggctacact agaaggacag tatttggtat ctgcgctctg    480
ctgaagccag ttaccttcgg aaaaagagtt ggtagctctt gatccggcaa acaaaccacc    540
gctggtagcg tggttttttt tgtttgcaag cagcagatta cgcgcagaaa aaaggatct    600 caagaagatc ctttgat                                                   617
```

<210> SEQ ID NO 4
<211> LENGTH: 660
<212> TYPE: DNA
<213> ORGANISM: Artificial Sequence
<220> FEATURE:
<223> OTHER INFORMATION: Lactic acid bacterial plasmid replicon

<400> SEQUENCE: 4

```
atggctaaag acaaggcaag gtacttcact ttttgctat atccggaaag tattccaaat     60
gattggaatc aacgcttgga actgatgggc gttcctattg cgattagtcc tctgcatgat    120
agggataaga gcaatgttga agggcagacg tacaagaaag ctcattatca tgttgtttat    180
gtggcaaaaa atcctgttac gacggatagc gttaggaaaa gaatccaaag ggctttgggg    240
cctagaagcg tttctaaagt gcaaattgtt gctcagagca tgaaaaatat gtatttgtat    300
ctgacacatg aatctaaaga cgctattgct aaaaataagc acaagtacag caagcacgac    360
attactttgc tgaacaattt tgatattgat cgctatatta cgcttgatgt tgaagacaaa    420
gacgacatgc tgaatgatgt ttgtgatttg attgatgacc ataatttggc aaatatgcgt    480
gaactgagac gcttttttaaa agctcatggt tcagaatatg gcatacccgg tattaaagtc    540
gtcaattcgg ttttacgtgc tcatactgga ctgataaggc tgtatttcga tgctgtttat    600
caggaacgca agtacggcag aggcgatata aacaaagaga ccggtgagat acaagactaa    660
```

<210> SEQ ID NO 5
<211> LENGTH: 248
<212> TYPE: DNA
<213> ORGANISM: Artificial Sequence
<220> FEATURE:
<223> OTHER INFORMATION: E. coli repressor of primer

<400> SEQUENCE: 5

```
gtgtatactg gcttaactat gcggcatcag agcagattgt actgagagtg caccattgcg     60
gtgtgaaata ccgcacagat gcgtaaggag aaaataccgc atcaggcgct cttccgcttc    120
ctcgctcact gactcgctgc gctcggtcgt tcggctgcgg cgagcggtat cagctcactc    180
aaaggcggta atacggttat ccacagaatc agggggataac gcaggaaaga acatgtgagc    240
aaaaggcc                                                            248
```

<210> SEQ ID NO 6
<211> LENGTH: 1764
<212> TYPE: DNA
<213> ORGANISM: Artificial Sequence
<220> FEATURE:
<223> OTHER INFORMATION: Lactic acid bacterial region

<400> SEQUENCE: 6

```
gaattcgcaa tgcgcactta cactccaaat aaattggagt tgtgctaaaa cacttaaacc     60
```

| | |
|---|---|
| tgtatcagaa gtcggctagc cgacaacaaa aaaggcgctc aattgagcac ccaatttca | 120 |
| tttgctaatt agtcttgtat ctcaccggtc tctttgttta tatcgcctct gccgtacttg | 180 |
| cgttcctgat aaacagcatc gaaatacagc cttatcagtc cagtatgagc acgtaaaacc | 240 |
| gaattgacga ctttaatacc gggtatgcca tattctgaac catgagcttt taaaaagcgt | 300 |
| ctcagttcac gcatatttgc caattatgg tcatcaatca aatcacaaac atcattcagc | 360 |
| atgtcgtctt tgtcttcaac atcaagcgta atatagcgat caatatcaaa attgttcagc | 420 |
| aaagtaatgt cgtgcttgct gtacttgtgc ttattttag caatagcgtc tttagattca | 480 |
| tgtgtcagat acaaatacat attttttcatg ctctgagcaa caatttgcac tttagaaacg | 540 |
| cttctaggcc ccaaagccct ttggattctt ttcctaacgc tatccgtcgt aacaggattt | 600 |
| tttgccacat aaacaacatg ataatgagct ttcttgtacg tctgcccttc aacattgctc | 660 |
| ttatccctat catgcagagg actaatcgca ataggaacgc ccatcagttc caagcgttga | 720 |
| ttccaatcat ttggaatact ttccggatat agcaaaaaag tgaagtacct tgccttgtct | 780 |
| ttagccataa tgttaaaatc gccttatcag aataagcaac aatcgagcga acttttcagc | 840 |
| gggtacgctc ttttttttgtg ctcatttctg cccttccttg tattttttcta gtgcaactgt | 900 |
| aatcaatgca gatttagata acctttgtt tttcgcagtc tccgacaaat attcaagaac | 960 |
| ttgactcgat aacgtaatcg tcaatctctt tttactttcc aaaatttcta acctccttca | 1020 |
| aatattcact aaagaaaaag tagcataatt acgtatttaa tgcaacaaaa tacgtattaa | 1080 |
| attcaaaaaa atcaccaaaa tgtcgccaaa atgtcgctca ataataaagt ggactaatcc | 1140 |
| cttgggagag tagacctgaa gccacctaaa attcagtttt ggcactcggc acttaaaggg | 1200 |
| ggggtcgtag tacggtcgca aaattcgctc cctcgccccc cctgattttc aaatttctat | 1260 |
| cccacacgaa taaaccatg ggcgctgccc aaacccgcaa gctgtgtcag cttgacccca | 1320 |
| taaatgagcg ggagctcccg ctcaaactca ccctgcactc gccgtgaggc aggcaaaaaa | 1380 |
| agcaggtgtg cttttctttg catgcgcaaa agtgtcttgg tctagtgagt ctgtcaactc | 1440 |
| cttaaagcct cctagaacgg ctaaaagccg ttctacgtcg atttaccgtt gacggacagt | 1500 |
| aaattatacg gttaacagct aaaatggctt agagagcaaa ttaggggcat ttaaagccaa | 1560 |
| tctttaaagc caataaagtc cgaaggagtt ggcgactgga cttattggc tttaaagatt | 1620 |
| ccaactgacg caagtcagtt tgtttgagc aaagcgaaat ctgatacagt tttaatgggt | 1680 |
| ttagcacagc gtcatctttg atgacgtgta agtgtacctt tgacatttc ttcggatttt | 1740 |
| ttcattgcta ttttttaaaag atct | 1764 |

<210> SEQ ID NO 7
<211> LENGTH: 1466
<212> TYPE: DNA
<213> ORGANISM: Artificial Sequence
<220> FEATURE:
<223> OTHER INFORMATION: E. coli region

<400> SEQUENCE: 7

| | |
|---|---|
| ggtaccaaag catgcaatga gctcagtaac ccgtatcgtg agcatcctct ctcgtttcat | 60 |
| cggtatcatt accccatga acagaaatcc cccttacacg gaggcatcag tgaccaaaca | 120 |
| ggaaaaaacc gcccttaaca tggcccgctt tatcagaagc cagacattaa cgcttctgga | 180 |
| gaaactcaac gagctggacg cggatgaaca ggcagacatc tgtgaatcgc ttcacgacca | 240 |
| cgctgatgag ctttaccgca gctgcctcgc gcgtttcggt gatgacggtg aaaacctctg | 300 |
| acacatgcag ctcccggaga cggtcacagc ttgtctgtaa gcggatgccg ggagcagaca | 360 |

```
agcccgtcag ggcgcgtcag cgggtgttgg cgggtgtcgg ggcgcagcca tgacccagtc    420
acgtagcgat agcggagtgt atactggctt aactatgcgg catcagagca gattgtactg    480
agagtgcacc attgcggtgt gaaataccgc acagatgcgt aaggagaaaa taccgcatca    540
ggcgctcttc cgcttcctcg ctcactgact cgctgcgctc ggtcgttcgg ctgcggcgag    600
cggtatcagc tcactcaaag gcggtaatac ggttatccac agaatcaggg gataacgcag    660
gaaagaacat gtgagcaaaa ggccagcaaa aggccaggaa ccgtaaaaag ccgcgttgc    720 tggcgttttt ccataggctc cgccccctg acgagcatca caaaaatcga cgctcaagtc    780
agaggtggcg aaacccgaca ggactataaa gataccaggc gtttccccct ggaagctccc    840
tcgtgcgctc tcctgttccg accctgccgc ttaccggata cctgtccgcc tttctccctt    900
cgggaagcgt ggcgctttct catagctcac gctgtaggta tctcagttcg gtgtaggtcg    960
ttcgctccaa gctgggctgt gtgcacgaac cccccgttca gcccgaccgc tgcgccttat   1020
ccggtaacta tcgtcttgag tccaacccgg taagacacga cttatcgcca ctggcagcag   1080
ccactggtaa caggattagc agagcgaggt atgtaggcgg tgctacagag ttcttgaagt   1140
ggtggcctaa ctacggctac actagaagga cagtatttgg tatctgcgct ctgctgaagc   1200
cagttacctt cggaaaaaga gttggtagct cttgatccgg caaacaaacc accgctggta   1260
gcggtggttt ttttgtttgc aagcagcaga ttacgcgcag aaaaaaagga tctcaagaag   1320
atcctttgat cttttctacg gggtctgacg ctcagtggaa cgaaaactca cgttaaggga   1380
ttttggtcat gaacaataaa actgtctgct tacataaaca gtaatacaag gggtgttatg   1440
agccatatca acgggaaacg ctcgag                                         1466

<210> SEQ ID NO 8
<211> LENGTH: 26
<212> TYPE: DNA
<213> ORGANISM: Artificial Sequence
<220> FEATURE:
<223> OTHER INFORMATION: Primer pJET1.2NEWF

<400> SEQUENCE: 8
ggcgtaatac gactcactat agggag                                           26

<210> SEQ ID NO 9
<211> LENGTH: 24
<212> TYPE: DNA
<213> ORGANISM: Artificial Sequence
<220> FEATURE:
<223> OTHER INFORMATION: Primer pJET1.2NEWR

<400> SEQUENCE: 9
catcgatttt ccatggcagc tgag                                             24

<210> SEQ ID NO 10
<211> LENGTH: 27
<212> TYPE: DNA
<213> ORGANISM: Artificial Sequence
<220> FEATURE:
<223> OTHER INFORMATION: Primer pLP31-8 check F

<400> SEQUENCE: 10
gattagtcct ctgcatgata gggataa                                          27

<210> SEQ ID NO 11
<211> LENGTH: 24
<212> TYPE: DNA
```

<213> ORGANISM: Artificial Sequence
<220> FEATURE:
<223> OTHER INFORMATION: Primer pLP31-8 check R

<400> SEQUENCE: 11
tttcatgctc tgagcaacaa tttg                                          24

<210> SEQ ID NO 12
<211> LENGTH: 39
<212> TYPE: DNA
<213> ORGANISM: Artificial Sequence
<220> FEATURE:
<223> OTHER INFORMATION: Primer pLP31-8F

<400> SEQUENCE: 12
gatataagat cttttaaaaa tagcaatgaa aaaatccga                          39

<210> SEQ ID NO 13
<211> LENGTH: 31
<212> TYPE: DNA
<213> ORGANISM: Artificial Sequence
<220> FEATURE:
<223> OTHER INFORMATION: Primer pLP31-8M2

<400> SEQUENCE: 13
ccccaaagcc ctttggattc ttttcctaac g                                  31

<210> SEQ ID NO 14
<211> LENGTH: 31
<212> TYPE: DNA
<213> ORGANISM: Artificial Sequence
<220> FEATURE:
<223> OTHER INFORMATION: Primer pLP31-8M1

<400> SEQUENCE: 14
cgttaggaaa agaatccaaa gggctttggg g                                  31

<210> SEQ ID NO 15
<211> LENGTH: 33
<212> TYPE: DNA
<213> ORGANISM: Artificial Sequence
<220> FEATURE:
<223> OTHER INFORMATION: Primer pLP31-8R

<400> SEQUENCE: 15
caatatgaat tcgcaatgcg cacttacact cca                                33

<210> SEQ ID NO 16
<211> LENGTH: 20
<212> TYPE: DNA
<213> ORGANISM: Artificial Sequence
<220> FEATURE:
<223> OTHER INFORMATION: Primer LPTufF

<400> SEQUENCE: 16
ttcctgttat ccgtggttca                                               20

<210> SEQ ID NO 17
<211> LENGTH: 20
<212> TYPE: DNA
<213> ORGANISM: Artificial Sequence
<220> FEATURE:
<223> OTHER INFORMATION: Primer LPTufR

<400> SEQUENCE: 17
aacaggcatc aagaaaggct                                               20

<210> SEQ ID NO 18
<211> LENGTH: 20
<212> TYPE: DNA
<213> ORGANISM: Artificial Sequence
<220> FEATURE:
<223> OTHER INFORMATION: Primer LGGTufF

<400> SEQUENCE: 18
accttggatc ttggtgaagc                                              20

<210> SEQ ID NO 19
<211> LENGTH: 20
<212> TYPE: DNA
<213> ORGANISM: Artificial Sequence
<220> FEATURE:
<223> OTHER INFORMATION: Primer LGGTufR

<400> SEQUENCE: 19
tcaacttggt cacggttgat                                              20

<210> SEQ ID NO 20
<211> LENGTH: 19
<212> TYPE: DNA
<213> ORGANISM: Artificial Sequence
<220> FEATURE:
<223> OTHER INFORMATION: Primer PepXF

<400> SEQUENCE: 20
gggacaaaca tgcgttact                                               19

<210> SEQ ID NO 21
<211> LENGTH: 20
<212> TYPE: DNA
<213> ORGANISM: Artificial Sequence
<220> FEATURE:
<223> OTHER INFORMATION: Primer PepXR

<400> SEQUENCE: 21
ttcacgaccg attagaacca                                              20

<210> SEQ ID NO 22
<211> LENGTH: 20
<212> TYPE: DNA
<213> ORGANISM: Artificial Sequence
<220> FEATURE:
<223> OTHER INFORMATION: Primer AmyF

<400> SEQUENCE: 22
ttcctgttat ccgtggttca                                              20

<210> SEQ ID NO 23
<211> LENGTH: 20
<212> TYPE: DNA
<213> ORGANISM: Artificial Sequence
<220> FEATURE:
<223> OTHER INFORMATION: Primer AmyR

<400> SEQUENCE: 23
aacaggcatc aagaaaggct                                              20

<210> SEQ ID NO 24
<211> LENGTH: 20
<212> TYPE: DNA
<213> ORGANISM: Artificial Sequence
<220> FEATURE:
<223> OTHER INFORMATION: Primer pLP31-8RTF

```
<400> SEQUENCE: 24
gcgagtgcag ggtgagtttg                                                20

<210> SEQ ID NO 25
<211> LENGTH: 20
<212> TYPE: DNA
<213> ORGANISM: Artificial Sequence
<220> FEATURE:
<223> OTHER INFORMATION: Primer pLP31-8RTR

<400> SEQUENCE: 25
gggtcgtagt acggtcgcaa                                                20
```

SHUTTLE VECTOR, PROKARYOTIC HOST CELLS, KIT, AND METHOD FOR PRODUCING PROTEINS

BACKGROUND

Technical Field

The present application relates to a vector used in genetic engineering, particularly a shuttle vector that can replicate in various hosts.

Description of Related Art

A plasmid is an extrachromosomal genetic material in a microorganism and is commonly used in genetic engineering as a vector for delivering and expressing exogenous genes in a host cell. Current plasmid-related studies basically cover eight research areas, including plasmid isolation and sequencing, physiological roles of plasmids, replication mode of plasmid, plasmid incompatibility, host range of plasmids, plasmid stability, plasmid copy number in a host, and construction of plasmid-based vectors used in genetic engineering, such as shuttle vectors, cloning vectors and expression vectors.

Shuttle vectors, among all, refer to a type of plasmids that are able to replicate in at least two phylogenetically different species. The shuttle vector pHY300PLK for *Escherichia coli* and *Bacillus subtilis*, for example, is composed of the site of replication of *E. coli* plasmid pACYC177 and that of *Enterococcus faecalis* DS-5 plasmid pAMα1, and can be transformed into *E. coli* and *B. subtilis*. Given their ability to replicate in various species, shuttle vectors can facilitate genetic manipulation in an effective way. For example, gene cloning can be carried out in *E. coli* that is easy to manipulate, and the obtained shuttle vectors containing correct gene fragments are then transformed into another host for gene expression. Since shuttle vectors are convenient to be used in two or more hosts for genetic manipulation, there is a constant demand in the art for multiple novel shuttle vectors that can meet research and commercial needs.

SUMMARY

Accordingly, one object of the present application is to provide a novel shuttle vector able to be used at least in a *Lactobacillus* prokaryotic cell and in another non-*Lactobacillus* prokaryotic cells, so as to meet needs in the art. In a preferred embodiment, the *Lactobacillus* prokaryotic cells are *Lactobacillus plantarum*, *Lactobacillus rhamnosus* (LGG) or *Weissella cibaria*, and the non-*Lactobacillus* prokaryotic cells may include *Escherichia coli*, *Bacillus subtilis* or the like.

In one aspect, the shuttle vector may comprise: (a) an *E. coli* plasmid replicon gene comprising SEQ ID NO: 3; and (b) a *Lactobacillus* plasmid replicon gene comprising SEQ ID NO: 4.

Preferably, the shuttle vector may comprise SEQ ID NO: 2. In one embodiment, the vector is pBRLP31-8.

Preferably, said shuttle vector further comprises a single-strand origin (sso) and a double-strand origin (dso).

Preferably, the shuttle vector further comprises a multiple cloning site useful for cloning a target gene. In one possible embodiment, the multiple cloning site further comprises an expression element at upstream thereof.

Preferably, the shuttle vector further comprises a selectable marker. In one embodiment, said selectable marker is an antibiotic resistance marker gene, a non-antibiotic resistance marker gene, or a combination thereof. In a preferred embodiment, said selectable marker is a chloramphenicol resistance gene.

Preferably, the shuttle vector can replicate in *E. coli, L. plantarum, L. rhamnosus* (LGG), *W. cibaria, B. subtilis* or a combination thereof.

Preferably, the shuttle vector further comprises a gene encoding *E. coli* repressor of primer. In one embodiment, the gene encoding *E. coli* repressor of primer comprises SEQ ID NO: 5.

Another object of the present application is to provide a shuttle vector that may comprise: a *Lactobacillus* region, which may comprise SEQ ID NO: 6; and an *E. coli* region, which may comprise SEQ ID NO: 7. In one embodiment, said *Lactobacillus* region comprises a single-strand origin, a double-strand origin and a *Lactobacillus* plasmid replicon gene. In another embodiment, said *E. coli* region comprises an *E. coli* plasmid replicon gene and a gene encoding *E. coli* repressor of primer.

Preferably, the *E. coli* plasmid replicon gene may be the rep of *E. coli* plasmid pBR322, or the gene encoding *E. coli* repressor of primer may be the rop of *E. coli* plasmid pBR322.

Preferably, the shuttle vector further comprises a selectable marker, which may be an antibiotic resistance marker gene, a non-antibiotic resistance marker gene, or a combination thereof. In one embodiment, said selectable marker may be a chloramphenicol resistance gene.

Preferably, the shuttle vector further comprises a multiple cloning site useful for cloning a target gene. In one possible embodiment, the multiple cloning site further comprises an expression element at upstream thereof.

Another object of the present application is to provide a prokaryotic host cell comprising the shuttle vector.

Preferably, the prokaryotic host cells may include *E. coli, L. plantarum, L. rhamnosus* (LGG), *W. ciboria* or *B. subtilis*.

Still another object of the present application is to provide a method for producing proteins using the prokaryotic host cell. The method comprises the following steps: transferring said prokaryotic host cell into a culture medium and causing the cell to express said proteins under appropriate culture conditions; and recovering proteins from the prokaryotic host cell or from the broth of said prokaryotic host cell.

Preferably, the method may further comprise constructing the shuttle vector containing a target gene.

Preferably, the method may further comprise transforming the prokaryotic host cell using said shuttle vector.

An object of the present application is to provide a kit that could be used to express exogenous genes, the kit comprising said shuttle vector.

In other words, the present application constructs a novel shuttle vector pBRLP31-8 using the minimal cryptic plasmid pLP31-8 of *Lactobacillus* ATIT-031 isolated from miso, as well as the replication region of *E. coli* plasmid pBR322. In one embodiment, the EcoR1 cutting site present on the site of replication in pLP31-8 can be modified via PCR-based site-directed mutagenesis so that the vector produced no longer contains the EcoR1 cutting site, thereby developing into a shuttle vector suitable for genetic manipulation.

In addition, a shuttle vector constructed based on one example of the present application may be used to transform at least *E. coli, L. plantarum, L. rhamnosus* (LGG), *W. cibaria* or *B. subtilis*, and the shuttle vector can then replicate therein. This suggests the shuttle vector can indeed be used for developing multi-host expression systems to meet research and commercial needs.

DETAILED DESCRIPTION

Figure 1:
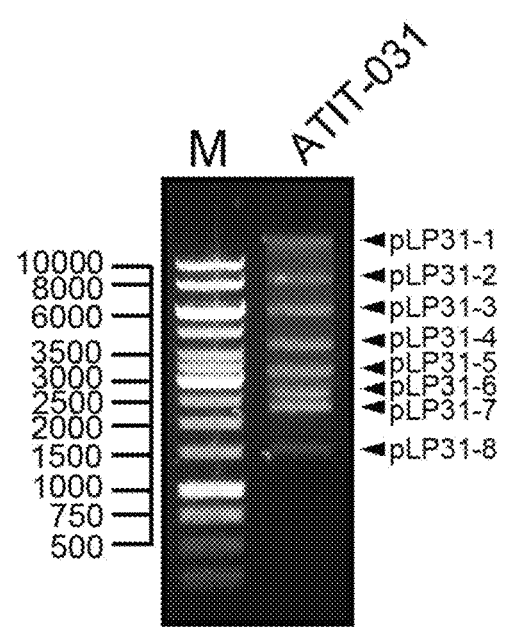
FIG. 1 illustrates a gel electrophoresis result of *L. plantarum* ATIT-031 plasmids, wherein Lane M represents 1 kb DNA Ladder.

Unless otherwise defined, all technical and scientific terms used herein have the same meaning as understood by a person having ordinary skill in the art. In the case where differences in interpretations arise, the definitions provided herein shall apply.

Unless otherwise specified, all percentages, portions and proportions are determined by weight.

As used herein, the term "produced from" has the same meaning as "comprising." As used herein, the terms "includes," "including," "comprises," "comprising." "has," "having," "contains," "containing" or other variants are intended to cover terms that are inclusive and non-excluding. For example, a composition, process, method, product or device that contains a plurality of elements on the list may not be limited to the listed elements, but rather comprises other non-listed elements that are inherent in the composition, process, method, product or device. The term "include" or "including" is generally used in the sense of "comprise" or "comprising," which denotes the presence of one or more characteristics or components.

The object of the present application is to provide a shuttle vector, which can replicate at least in a *Lactobacillus* cell and in another non-*Lactobacillus* prokaryotic cell. The shuttle vector has the advantage in genetic engineering as it is able to replicate in two or more host cells.

In one embodiment, a shuttle vector is provided, comprising: (a) an *E. coli* plasmid replicon gene comprising SEQ ID NO: 3; and (b) a *Lactobacillus* plasmid replicon gene comprising SEQ ID NO: 4. In a preferred embodiment, a shuttle vector may comprise SEQ ID NO: 2. In one embodiment, the shuttle vector is named pBRLP31-8.

| SEQ ID NO | DESCRIPTION | SEQUENCE |
|---|---|---|
| 3 | E. coli plasmid replicon | GCGTTGCTGGCGTTTTTCCATAGGCTCCGCCCCCCTGACGAGCATC ACAAAAATCGACGCTCAAGTCAGAGGTGGCGAAACCCGACAGGA CTATAAAGATACCAGGCGTTTCCCCCTGGAAGCTCCCTCGTGCGCT CTCCTGTTCCGACCCTGCCGCTTACCGGATACCTGTCCGCCTTTTCTC CCTTCGGGAAGCGTGGCGCTTTCTCATAGCTCACGCTGTAGGTATC TCAGTTCGGTGTAGGTCGTTCGCTCCAAGCTGGGCTGTGTGCACGA ACCCCCCGTTCAGCCCGACCGCTGCGCCTTATCCGGTAACTATCGT CATGAGTCCAACCCGGTAAGACACGACTTATCGCCACTGGCAGCA GCCACTGGTAACAGGATTAGCAGAGCGAGGTATGTAGGCGGTGCT ACAGAGTTCTTGAAGTGGTGGCCTAACTACGGCTACACTAGAAGG ACAGTATTTGGTATCTGCGCTCTGCTGAAGCCAGTTACCTTCGGAA AAAGAGTTGGTAGCTCTTGATCCGGCAAACAAACCACCGCTGGTA GCGGTGGTTTTTTTGTTTGCAAGCAGCAGATTACGCGCAGAAAAA AAGGATCTCAAGAAGATCCTTTGAT |
| 4 | Lactobacillus plasmid replicon | ATGGCTAAAGACAAGGCAAGGTACTTCACTTTTTTGCTATATCCGG AAAGTATTCCAAATGATTGGAATCAACGCTTGGAACTGATGGGCG TTCCTATTGCGATTAGTCCTCTGCATGATAGGGATAAGAGCAATGT TGAAGGGCAGACGTACAAGAAAGCTCATTATCATGTTGTTTATGT GGCAAAAAATCCTGTTACGACGGATAGCGTTAGGAAAAGAATCCA AAGGGCTTTGGOGCCTAGAAGCGTTTCTAAAGTGCAAATTGTTGC TCAGAGCATGAAAAATATGTATTTGTATCTGACACATGAATCTAA AGACGCTATTGCTAAAAATAAGCACAAGTACAGCAAGCACGACAT TACTTTGCTGAACAATTTTGATATTGATCGCTATATTACGCTTGAT GTTGAAGACAAAGACGACATGCTGAATGATGTTTGTGATTTGATT GATGACCATAATTTGGCAAATATGCGTGAACTGAGACGCTTTTA AAAGCTCATGGTTCAGAATATGGCATACCCGGTATTAAAGTCGTC AATTCGGTTTTACGTGCTCATACTGGACTGATAAGGCTGTATTTCG ATGCTGTTTATCAGGAACGCAAGTACGGCAGAGGCGATATAAACA AAGAGACCGGTGAGATACAAGACTAA |

In another embodiment, a shuttle vector is provided that may comprise: a *Lactobacillus* region, which may comprise SEQ ID NO: 6; and an *E. coli* region, which may comprise SEQ ID NO: 7. In one embodiment, said *Lactobacillus* region comprises a single-strand origin, a double-strand origin and a *Lactobacillus* plasmid replicon gene; and said *E. coli* region comprises an *E. coli* plasmid replicon gene and a gene encoding *E. coli* repressor of primer. In a preferred embodiment, a gene encoding *E. coli* repressor of primer may comprise SEQ ID NO: 5.

| SEQ ID NO | DESCRIPTION | SEQUENCE |
|---|---|---|
| 5 | E. coli repressor of primer | GTGTATACTGGCTTAACTATGCGGCATCAGAGCAGATTGTACTGA GAGTGCACCATTGCGGTGTGAAATACCGCACAGATGCGTAAGGAG AAAATACCGCATCAGGCGCTCTTCCGCTTCCTCGCTCACTGACTCG CTGCGCTCGGTCGTTCGGCTGCGGCGAGCGGTATCAGCTCACTCA AAGGCGGTAATACGGTTATCCACAGAATCAGGGGATAACGCAGG AAAGAACATGTGAGCAAAAGGCC |
| 6 | Lactobacillus region | GAATTCGCAATGCGCACTTACACTCCAAATAAATTGGAGTTGTGCT AAAACACTTAAACCTGTATCAGAAGTCGGCTAGCCGACAACAAAA AAGGCGCTCAATTGAGCACCCAATTTTCATTTGCTAATTAGTCTTG TATCTCACCGGTCTCTTTGTTTATATCGCCTCTGCCGTACTTGCGTT CCTGATAAACAGCATCGAAATACAGCCTTATCAGTCCAGTATGAG CACGTAAAACCGAATTGACGACTTTAATACCGGGTATGCCATATT CTGAACCATGAGCTTTTAAAAAGCGTCTCAGTTCACGCATATTTGC CAAATTATGGTCATCAATCAAATCACAAACATCATTCAGCATGTC GTCTTTGTCTTCAACATCAAGCGTAATATAGCGATCAATATCAAAA TTGTTCAGCAAAGTAATGTCGTGCTTGCTGTACTTGTGCTTATTTTT AGCAATAGCGTCTTTAGATTCATGTGTCAGATACAAATACATATTT TTCATGCTCTGAGCAACAATTTGCACTTTAGAAACGCTTCTAGGCC CCAAAGCGCTTTGGATTCTTTTCCTAACGCTATCCGTCGTAACAGG ATTTTTTGCCACATAAACAACATGATAATGAGCTTTCTTGTACGTC TGCCCTTCAACATTGCTCTTATCCCTATCATGCAGAGGACTAATCG CAATAGGAACGCCCATCAGTTCCAAGCGTTGATTCCAATCATTTGG AATACTTTCCGGATATAGCAAAAAAGTGAAGTACCTTGCCTTGTCT TTAGCCATAATGTTAAAATCGCCTTATCAGAATAAGCAACAATCG AGCGAACTTTTCAGCGGGTACGCTCTTTTTTTGTGCTCATTTCTGCC CTTCCTTGTATTTTTCTAGTGCAACTGTAATCAATGCAGATTTAGA TAAACCTTTGTTTTTCGCAGTCTCCGACAAATATTCAAGAACTTGA CTCGATAACGTAATCGTCAATCTCTTTTTACTTTCCAAAATTTCTAA CCTCCTTCAAATATTCACTAAAGAAAAAGTAGCATAATTACGTATT TAATGCAACAAAATACGTATTAAATTCAAAAAAATCACCAAAATG TCGCCAAAATGTCGCTCAATAATAAAGTGGACTAATCCCTTGGGA GAGTAGACCTGAAGCCACCTAAAATTCAGTTTTGGCACTCGGCAC TTAAAGGGGGGGTCGTAGTACGGTCGCAAAATTCGCTCCCTCGCC CCCCCTGATTTTCAAATTTCTATCCCACACGAATAAAACCATGGGC GCTGCCCAAACCCGCAAGCTGTGTCAGCTTGACCCCATAAATGAG CGGGAGCTCCCGCTCAAACTCACCCTGCACTCGCCGTGAGGCAGG CAAAAAAAGCAGCTGTGCTTTTCTTTGCATGCGCAAAAGTGTCTTG GTCTAGTGAGTCTGTCAACTCCTTAAAGCCTCCTAGAACGGCTAAA AGCCGTTCTACGTCGATTTACCGTTGACGGACAGTAAATTATACGG TTAACAGCTAAAATGGCTTAGAGAGCAAATTAGGGGCATTTAAAG CCAATCTTTAAAGCCAATAAAGTCCGAAGGAGTTGGCGACTGGAC TTTATTGGCTTTAAAGATTCCAACTGACGCAAGTCAGTTTTGTTTG AGCAAAGCGAAATCTGATACAGTTTTAATGGGTTTAGCACAGCGT CATCTTTGATGACGTGTAAGTGTACCTTTGACATTTTCTTCGGATTT TTTCATTGGTATTTTTAAAAGATCT |
| 7 | E. coli region | GGTACCAAAGCATGCAATGAGCTCAGTAACCCGTATCGTGAGCAT CCTCTCTCGTTTCATCGGTATCATTACCCCCATGAACAGAAATCCC CCTTACACGGAGGCATCAGTGACCAAACAGGAAAAAACCGCCCT AACATGGCCCGCTTTATCAGAAGCCAGACATTAACGCTTCTGGAG AAACTCAACGAGCTGGACGCGGATGAACAGGCAGACATCTGTGA ATCGCTTCACGACCACGCTGATGAGCTTTACCGCAGCTGCCTCGCG CGTTTCGGTGATGACGGTGAAAACCTCTGACACATGCAGCTCCCG GAGACGGTCACAGCTTGTCTGTAAGCGGATGCCGGGAGCAGACAA GCCCGTCAGGGCGCGTCAGCGGGTGTTGGCGGGTGTCGGGGCGCA GCCATGACCCAGTCACGTAGCGATAGCGGAGTGTATACTGGCTTA ACTATGCGGCATCAGAGCAGATTGTACTGAGAGTGCACCATTGCG GTGTGAAATACCGCACAGATGCGTAAGGAGAAAATACCGCATCAG GCGCTCTTCCGCTTCCTCGCTCACTGACTCGCTGCGCTCGGTCGTT CGGCTGCGGCGAGCGGTATCAGCTCACTCAAAGGCGGTAATACGG TTATCCACAGAATCAGGGGATAACGCAGGAAAGAACATGTGAGC AAAAGGCCAGCAAAAGGCCAGGAACCGTAAAAGGCCGCGTTGC TGGCGTTTTTCCATAGGCTCCGCCCCCCTGACGAGCATCACAAAAA TCGACGCTCAAGTCAGAGGTGGCGAAACCCGACAGGACTATAAAG ATACCAGGCGTTTCCCCCTGGAAGCTCCCTCGTGCGCTCTCCTGTT CCGACCCTGCCGCTTACCGGATACCTGTCCGCCTTTCTCCCTTCGG GAAGCGTGGCGCTTTCTCATAGCTCACGCTGTAGGTATCTCAGTTC GGTGTAGGTCGTTCGCTCCAAGCTGGGCTGTGTGCACGAACCCCC CGTTCAGCCCGACCGCTGCGCCTTATCCGGTAACTATCGTCTTGAG TCCAACCCGGTAAGACACGACTTATCGCCACTGGCAGCAGCCACT |

| SEQ ID NO | DESCRIPTION | SEQUENCE |
|---|---|---|
| | | GGTAACAGGATTAGCAGAGCGAGGTATGTAGGCGGTGCTACAGA GTTCTTGAAGTGGTGGCCTAACTACGGCTACACTAGAAGGACAGT ATTTGGTATCTGCGCTCTGCTGAAGCCAGTTTACCTTCGGAAAAAGA GTTGGTAGCTCTTGATCCGGCAAACAAACCACCGCTGGTAGCGGT GGTTTTTTTGTTTGCAAGCAGCAGATTACGCGCAGAAAAAAAGGA TCTCAAGAAGATCCTTTGATCTTTTCTACGGGGTCTGACGCTCAGT GGAACGAAAACTCACGTTAAGGGATTTTGGTCATGAACAATAAAA CTTGTCTGCTTACATAAACAGTAATACAAGGGGTGTTATGAGCCAT ATCAACGGGAAACGCTCGAG |

In yet another embodiment, a prokaryotic host cell is provided, comprising said shuttle vector. In a possible embodiment, the prokaryotic host cell may include *E. coli* cell, *L. plantarum* cell, *L. rhamnosus* (LGG) cell, *W. cibaria* cell or *B. subtilis* cell.

As used herein, the terms "host," "host cell" and "recombinant host cell" may be interchangeable and may refer to prokaryotic cells. One or more plasmids described herein, or said plasmids that have been inserted genes to be expressed via a genetic engineering method may be introduced into the host cell. As a person having ordinary skill in the art understands, the above terms not only refer to specific cells, but also to their daughter cells or potential daughter cells. In the case where the daughter cells undergo changes due to the impact of mutation or environmental factors and thus differ substantially from their parent cells, they still fall within the scope of such terms as used herein.

As used herein, the term "*E. coli/Lactobacillus* shuttle vector" refers to a vector on which replication origins for *E. coli* plasmids and *Lactobacillus* plasmids co-exist and enable the vector to replicate and proliferate at least in *E. coli* and *Lactobacillus*, thereby overcoming the limitation concerning the bacteria species used for obtaining plasmids. Normally, the shuttle vector may contain a selectable marker, including, but not limited to, a kanamycin-resistance marker or a chloramphenicol-resistance marker. In addition, the vector may also contain a restriction enzyme cutting site useful for genetic manipulation. Preferably, the vector may further comprise a multiple cloning site for inserting genes to be expressed, and genes inserted into said multiple cloning site may be controlled by expression element. In a possible embodiment, expression element may contain a promoter, and the promoter is a constitutive promoter or an inducible promoter.

In a possible embodiment, said expression element may further comprise: a ribosome binding site, an operator, a transcription/translation enhancer sequence or a combination thereof. The expression element may include, but not limited to, *Lactobacillus* P23 expression element, *Streptococcus lactis* P2P expression element, *Streptococcus lactis* P32 expression element, *Streptococcus lactis* P59 expression element, *Streptococcus lactis* P6C expression element, the expression element of *Lactobacillus* gene encoding S-layer protein thereof, the expression element of *Lactobacillus* Tuf gene, Cytomegalovirus (CMV) expression element, simian virus 40 (SV40) expression element. Rous sarcoma virus (RSV) expression element, the expression element of gene encoding phosphoglycerate kinase (PGK), the expression element of gene encoding thymidine kinase (TK), the expression element of gene encoding elongation factor 1 alpha (EF-1a), the expression element of gene encoding ubiquitin, the expression element of gene encoding actin, or a combination thereof.

As used herein, the term "*Lactobacillus* region" refers to a region that can be recognized and expressed by *Lactobacillus*; as used herein, the term "*E. coli* region" refers to a region that can be recognized and expressed by *E. coli*.

As described herein, the "non-*Lactobacillus* prokaryotic cell" is selected from prokaryotic cells other than *Lactobacillus* (such as Gram-negative or Gram-positive bacteria). In a preferred embodiment, said non-*Lactobacillus* prokaryotic cell is a Gram-negative bacterial cell. In a possible embodiment, said Gram-negative bacterial cell is *E. coli*. A person having ordinary in the art should be able to understand that the non-*Lactobacillus* prokaryotic cell described herein may as well be a Gram-positive bacterial cell. In a possible embodiment, said Gram-positive bacterial cell is *B. subtilis*.

As used herein, the term "plasmid replicon" refers to a protein that enables the shuttle vector of the present invention to replicate in the expression system of a host. The term "plasmid replicon gene" or "gene encoding plasmid replicon" refers to a gene sequence encodes said plasmid replicon as the protein product obtained via transcription/translation processes thereof in an organism.

In a possible embodiment, a "*Lactobacillus* plasmid replicon gene" of said *Lactobacillus* region refers to a gene that can be recognized and then transcribed/translated by said *Lactobacillus*, wherein a *Lactobacillus* plasmid replicon produced via the transcription/translated processes is able to initiate the replication of said vector within *Lactobacillus*. In another possible embodiment, a shuttle vector may further comprise a single-strand origin and a double-strand origin, wherein the *Lactobacillus* plasmid replicon produced via the transcription/translated processes is able to initiate the replication of said plasmid at said double-strand origin to produce double-stranded DNAs and free single-stranded DNAs. The single-strand origin on the free single-stranded DNAs will form a secondary structure of stem-loop, which can be identified by the RNA polymerase of the host. A RNA primer is then synthesized on the stem-loop, while the host cell DNA polymerase starts the replication of DNA at the 3'-end of the RNA primer, thereby converting single-stranded DNAs into double-stranded DNAs.

In a possible embodiment, an "*E. coli* plasmid replicon gene" of said *E. coli* region refers to a gene that can be recognized and then transcribed/translated by *E. coli*, wherein a replication protein produced via the transcription/translation processes is able to initiate the replication of said vector within *E. coli*. Said *E. coli* plasmid replicon gene may include, but not limited to, rep from *E. coli* plasmid pBR322, ColE1, p15A, pBBR1, pSC101, R6K, RK2 or RSF1010.

In a possible embodiment, a "gene encoding a repressor of primer" of said *E. coli* region refers to a gene that can be recognized and then transcribed/translated by said *E. coli*, wherein the repressor of primer produced via the transcription/translation processes may regulate the copy number of said vector within *E. coli*. Said repressor of primer may include, but not limited to, rop of *E. coli* plasmid pBR322.

As described herein, the "gene to be expressed" varies according to a user's needs. For example, if a shuttle vector constructed based on one example of the present invention is used for producing a certain protein (insulin, for instance) in large amounts via genetic engineering methods, said gene to be expressed will be the nucleic acid sequence of the protein. Another example: if a shuttle vector constructed based on one example of the present invention is used as a vaccine, the protein product generated after the transcription/translation of said gene to be expressed in a host (a human, for example) should be able to induce immune responses (i.e. as an immunity-inducing agent). Said immunity-inducing agent may include, but not limited to, an antigenic peptide, a protein or a fragment thereof that belongs to a pathogen (germ, virus and parasite).

As described herein, the "selectable marker" is used to confirm that the host has been successfully transformed with said vector. Said selectable vector may include, but not limited to, an antibiotic resistance selectable marker, a non-antibiotic resistance selectable marker or a combination thereof. In a possible embodiment, said selectable marker may be an antibiotic resistance selectable marker. For example, said antibiotic resistance selectable marker is a chloramphenicol resistance gene. In this possible embodiment, a successfully transformed host (such as *E. coli* or *Lactobacillus*) having said vector would obtain the resistance to chloramphenicol and able to survive in an environment where chloramphenicol is present.

As described herein, the "non-antibiotic resistance selectable marker" refers to a gene that does not rely on resistance to antibiotics to confirm that the transformation is successful. Said non-antibiotic resistance selectable marker includes, but not limited to a nucleic acid sequence of β-galactosidase. In an embodiment wherein a nucleic acid sequence of β-galactosidase is used as a selectable marker, a successfully transformed strain will break down X-gal (5-bromo-4-chloro-3-indolyl-beta-D-galactopyranoside) into galactose and 5-bromo-4-chloro-3-hydroxyindole, and 5-bromo-4-chloro-3-hydroxyindole molecules will dimerize to form 5,5'-dibromo-4,4'-dichloro-indigo, thereby producing a insoluble and discernible blue product.

In a preferred embodiment, said non-antibiotic resistance selectable marker is a nutritional starvation selectable marker (such as thymidylate synthase gene thyA), carbohydrate metabolism gene (such as lacF and lacG, which are related to lactose metabolic pathways), bacteriocin resistance gene (such as nisin resistance gene), heavy metal resistance gene (such as cadmium resistance gene), gene of bile salt hydrolase, gene of α-galactosidase, gene of D-alanine racemase or gene of heat shock protein.

As used herein, the terms such as "transform," "transformed" or "introduce a nucleic acid into a host cell" refer to the application of any methods for introducing a foreign nucleic acid (such as a vector) into a host cell with or without the presence of accompanying substances. The terms "transform a cell" or "transformed cell" suggest that a foreign nucleic acid is introduced into the cell or its daughter cells so that the host cell contains the foreign nucleic acid. Once introduced into the host cell, the nucleic acid is integrated with the chromosome and becomes a fragment thereof, or remains as an extrachromosomal element, for the purpose of replication. Transformation of an appropriate host cell with, for example, an expression vector can be achieved using known methods in the art, such as electroporation and particle bombardment, or using chemical methods such as catalyzing the transformation process with calcium phosphate. These methods are described in, for example, Maniatis et al., Molecular Cloning: A Laboratory Manual (Cold Spring Harbor Laboratory, 1982), or Ausubel et al., Current Protocols in Molecular Biology (John Wiley and Sons, 1994).

The indefinite articles "a" and "an" that are placed before an element or a component herein are intended to describe the exemplary number of the element or the component (that is, the number of appearances) in a non-limiting manner. Therefore, the articles "a" and "an" should be construed as including one or at least one, and the singular form of the element or the component should also include plural referents unless they are clearly singular.

Unless otherwise described, the materials, methods and examples herein are merely illustrative and not intended to limit the present invention. Although similar or equivalent methods or materials may be used to implement or test the present invention, those described herein are more appropriate.

Examples: Strains, Culture Medium, Chemicals and Reagents

1. Strains

*L. plantarum* ATIT-031 isolated from miso was used as the subject for the study of plasmids. *E. coli* ECOS 9-5 (Yeastern, Taiwan) was used as the host cell for cloning DNA. *L. plantarum* ATIT-018 isolated from homemade pickled cabbage, *L. rhamnosus* (LGG) BCRC 16000, and *B. subtilis* DB430, as well as *W. cibaria* ATIT-044 isolated from peach marinade were used to carry out transformation tests on shuttle vectors.

2. Culture Medium

A deMan-Rogosa-Sharpe (MRS) culture medium (Merck, USA) was used for culturing *Lactobacillus*, and 5 μg/mL chloramphenicol or 1.5% (w/v) agar was added, where necessary, for preparing solid culture plate. A Luria-Bertani (LB) culture medium was used for culturing *E. coli*, and 25 μg/mL chloramphenicol or 1.5% agar was added, where necessary, for preparing solid culture plate. A Luria-Bertani (LB) or Select APS™ Super Broth culture medium was used for culturing *B. subtilis*, and 5 μg/mL chloramphenicol or 1.5% (w/v) agar was added, where necessary, for preparing solid culture plate. Both the culture medium and agar were purchased from BD, USA. The components of deMan-Rogosa-Sharpe (MRS) medium, Luria-Bertani (LB) medium and/or Select APS™ Super Broth medium as well as proportions thereof are known to a person having ordinary skill in the art, and can be slightly modified according to practices of each laboratory or its technicians.

3. Chemicals and Reagents

The chemicals used in the present study were reagent grade chemicals purchased from Sigma-Aldrich, Affymetrix or Amresco, USA. RNase A solution and DNeasy Blood & Tissue Kit were purchased from Qiagen, Germany; restriction enzymes, GeneRuler™ 1 kb DNA ladder, Dream taq DNA polymerase and CloneJET™ PCR cloning kit were purchased from Thermo Fisher Scientific, USA; 50× TAE buffer and 6× EZ-Vision™ loading buffer were purchased from Amresco, USA; T4 DNA ligase was purchased from Yeastern, Taiwan; Plasmid Miniprep Purification Kit II, PCR Clean Up Kit, Gel Elution Kit and PCR Master Mix II were purchased from GMbiolab Co, Ltd., Taiwan; GDP-HiFi DNA Polymerase was purchased from Genedirex, USA; and Faststart Universal SYBR Green Master (ROX) was purchased from Roche, USA.

Example 1: Extraction of Plasmids from *L. plantarum* ATIT-031

Given that low-molecular-weight plasmids are easy to manipulate, the isolation process in this example began with the smallest plasmid contained in said *L. plantarum* ATIT-031.

A single colony of *L. plantarum* ATIT-031 was chosen and an MRS liquid medium was inoculated with the colony. The medium was incubated at 30° C. for 16 hours, and the extraction of *L. plantarum* plasmids was performed using Plasmid Miniprep Purification Kit II in a process modified from the manufacturer's protocol. The solution II, solution III, washing solution A, washing solution B and elution solution mentioned in the process were all reagents included in the kit. In short, 2 mL broth cultured overnight was put into a microcentrifuge tube, pellet was collected by centrifugation (21,910×g, 5 minutes, 4° C.), the supernatant was discarded, and the previous steps were repeated once. The pellet obtained was suspended in 1.0 mL TSE buffer (10 mM Tris-HCL, 10 mM EDTA, 300 mM NaCl, pH 8.0) and pellet was re-collected by centrifugation (21.910×g, 5 minutes, 4° C.) while the supernatant was discarded. The collected pellet was re-suspended in 200 μL *Lactobacillus* plasmid solution I (50 mM Tris-HCl, 10 mM EDTA, 25% sucrose, pH 8.0; 30 mg/mL lysozyme and 100 μg/mL RNase A were added additionally) at 37° C. for 30 minutes. 200 μL solution II was added to the tube and mixed gently several times. 200 μL solution III was added into the resulting mixture and mixed gently several times. The tubes were centrifuged (21,910×g, 10 minutes, room temperature) and the supernatant was collected.

A spin column was placed in a collection tube, filled with the collected supernatant, and centrifuged (21,910×g, 2 minutes, room temperature). After centrifugation, the filtrate was discarded. 500 μL washing solution A was added to the spin column for re-centrifugation (21,910×g, 2 minutes, room temperature). After re-centrifugation, the filtrate was discarded. These steps effectively reduced endonuclease contamination. 600 μL washing solution B was immediately added to the spin column for another centrifugation (21,910×g, 2 minutes, room temperature), and the filtrate was discarded (this step was repeated twice). The centrifugation was continued (21,910×g, 5 minutes, room temperature) in order to remove residual alcohol. Finally, the spin column was placed in a sterile microcentrifuge tube and centrifuged (21,910×g, 2 minutes, room temperature) after 40 μL dissolution medium was appropriately added for extraction of plasmid DNA. The extracted plasmids were stored at −20° C. for future use.

Example 2: Isolation of Plasmids from *L. plantarum* ATIT-031 Using Agarose Gel Electrophoresis, and Recovering of Target Plasmids pLP31-8

0.7% agrose (Affymetrix, USA) gel was used as the medium for electrophoresis, and 0.5× TAE buffer was used as the buffer solution in electrophoresis. DNA samples were mixed with 6× EZ-Vision™ loading buffer at a ratio of 5:1, and the resulting mixture was loaded into the wells in the agarose gel. The electrophoresis was performed at 110V, and result thereof was observed using a ultra-violet transilluminator. Bands to be analyzed were cut out of the gel. The bands to be analyzed were plasmids of lowest molecular weight; therefore, among all bands that were cut from the gel, those of longest migration distance represented plasmids pLP31-8, the smallest plasmids in *L. plantarum* ATIT-031 as shown in FIG. 1.

The target plasmids pLP31-8 were recovered from the gel using Gel Elution Kit according to the manufacturer's protocol as detailed below. The agarose gel containing the DNA fragments to be recovered was put into a microcentrifuge tube. 0.5 mL GEX buffer was added to the tube and left for reaction at 60° C. for 10 minutes until the gel was dissolved completely. Once cooled, the solution was filled into the microcentrifuge tube for centrifugation (21,910×g, 1 minute), resulting in that DNA in the solution bound onto the resin of the tube. 0.5 mL WF buffer was filled into a spin column for centrifugation (21,910×g, 1 minute, room temperature), and the effluent was discarded after centrifugation. 0.7 mL WS buffer was further added to the tube for centrifugation (21,910×g, 1 minute, room temperature), and the effluent was discarded after centrifugation; these steps were repeated once in order to remove salt impurities from the resin. To prevent residual alcohol from interfering the subsequent steps of the experiment, the spin column was re-centrifuged at 21,910×g for 5 minutes. Finally, the spin column was inserted into a sterile centrifuge tube, and an appropriate amount of dissolution medium was added to the spin column and centrifuged (21,910×g, 2 minutes, room temperature) for extraction of the plasmid DNA.

Example 3: DNA Cloning and Sequencing of Plasmid pLP31-8

The plasmid pLP31-8 was cleaved with restriction enzyme EcoRI and analyzed by agarose gel electrophoresis, and plasmid DNA was recovered from the gel using Gel Elution Kit. Fill-in reactions and blunt-end cloning were performed on the recovered plasmid DNA using Clone-JET™ PCR cloning kit according to the manufacturer's protocol. *E. coli* ECOS 9-5 was transformed with the annealed product of pLP31-8 DNA fragments and cloning vector pJET1.2. Colony polymerase chain reactions were performed using primers pJET1.2NEWF (as shown in SEQ ID NO: 8)/pJET1.2NEWR (as shown in SEQ ID NO: 9) in conjunction with Dream taq DNA polymerase, so as to select transformants that may contain pLP31-8 DNA fragments. Two transformants were randomly selected for culture, and extraction of plasmids was performed using Plasmid Miniprep Purification Kit II. The extracted DNA was sent to Tri-I Biotech for sequencing. Based on the sequencing results, primers pLP31-8 check F (as shown in SEQ ID NO: 10) and pLP31-8 check R (as shown in SEQ ID NO: 11) were designed for confirming that the complete sequence had been obtained. Polymerase chain reactions (PCR) were performed using a primer combination of pLP31-8 check F/pLP31-8 check R, GDR-HiFi DNA Polymerase and plasmid pLP31. Once recovering using PCR Clean-up kit, PCR products were cloned using CloneJET™ PCR cloning kit. A partial sequence of pLP31-8 was able to be obtained from performing colony polymerase chain reactions, extracting plasmid DNA from transformants, as well as sequencing DNA. The complete sequence was able to be obtained by comparing the partial sequence with said sequencing results of pLP31-8 DNA.

| SEQ ID NO | DESCRIPTION | SEQUENCE |
|---|---|---|
| 8 | pJET1.2NEWF | GGCGTAATACGACTCACTATAGGGAG |
| 9 | pJET1.2NEWR | CATCGATTTTCCATGGCAGCTGAG |

The sequencing results of pLP31-8 showed that the plasmid was 1,753 bp in length, with a GC content of 45%. It could be predicted by the NCBI ORF finder that the plasmid contained an open reading frame of 660 bp in length. The results of a comparative analysis on amino acid homology in the ORF showed that the ORF was predicted to be a rep that bore a relation to replication of plasmids as well as a similarity of 88% to the rep sequence of *Lactobacillus helveticus* plasmid pLH2. A single strand orign (sso) and a double-strand origin (dso) were identified in the upstream of the rep. See FIG. 2 for the physical map of plasmid pLP31-8, and SEQ ID NO: 1 for its sequence.

| SEQ ID NO | DESCRIPTION | SEQUENCE |
|---|---|---|
| 1 | Complete sequence of pLP31-8 | TTTAAAAATAGCAATGAAAAAATCCGAAGAAAATGTCAAAGGTAC ACTTACACGTCATCAAAGATGACGCTGTGCTAAACCCATTAAAACC TGTATCAGATTTCGCTTTGCTCAAACAAAACTGACTTGCGTCAGTT GGAATCTTTAAAGCCAATAAAGTCCAGTCGCCAACTCCTTCGGACT TTATTGGCTTTAAAGATTGGCTTTAAATGCCCCTAATTTGCTCTCTAA GCCATTTTAGCTGTTAACCGTATAATTTACTGTCCGTCAACGGTAAA TCGACGTAGAACGGCTTTTAGCCGTTCTAGGAGGCTTTAAGGAGTT GACAGACTCACTAGACCAAGACACTTTTGCGCATGCAAAGAAAAG CACACCTGCTTTTTTTGCCTGCCTCACGGCGAGTGCAGGGTGAGTT TGAGCGGGAGCTCCCGCTCATTTATGGGGTCAAGCTGACACAGCTT GCGGGTTTGGGCAGCGCCCATGGTTTTATTCGTGTGGGATAGAAAT TTGAAAATCAGGGGGGCGAGGGAGCGAATTTTGCGACCGTACTA CGACCCCCCTTTAAGTGCCGAGTGCCAAAACTGAATTTTAGGTGG CTTCAGGTCTACTCTCCCAAGGGATTAGTCCACTTTATTATTGAGCG ACATTTTGGCGACATTTTGGTGATTTTTTTGAATTTAATACGTATTTT GTTGCATTAAATACGTAATTATGCTACTTTTTCTTTAGTGAATATTTG AAGGAGGTTAGAAATTTTGGAAAGTAAAAAGAGATTGACGATTAC GTTATCGAGTCAAGTTCTTGAATATTTGTCGGAGACTGCGAAAAAC AAAGGTTTATCTAAATCTGCATTGATTACAGTTGCACTAGAAAATA CAAGGAAGGGCAGAAATGAGCACAAAAAAAGAGCGTACCCGCTG AAAAGTTCGCTCGATTGTTGCTTATTCTGATAAGGCGATTTTAACAT TATGGCTAAAGACAAGGCAAGGTACTTCACTTTTTTGCTATATCCGG AAAGTATTCCAAATGATTGGAATCAACGCTTGGAACTGATGGGCGT TCCTATTGCGATTAGTCCTCTGCATGATAGGGATAAGAGCAATGTTG AAGGGCAGACGTACAAGAAAGCTCATTATCATGTTGTTTATGTGGC AAAAAATCCTGTTACGACGGATAGCGTTAGGAAAAGAATCCAAAG GGCTTTGGGGCCTAGAAGCGTTTCTAAAGTGCAAATTGTTGCTCAG AGCATGAAAAATATGTATTTGTATCTGACACATGAATCTAAAGACGC TATTGCTAAAAATAAGCACAAGTACAGCAAGCACGACATTACTTTG CTGAACAATTTTGATATTGATCGCTATATTACGCTTGATGTTGAAGAC AAAGACGACATGCTGAATGATGTTTGTGATTTGATTGATGACCATAA TTTGGCAAATATGCGTGAACTGAGCGCTTTTTAAAAGCTCATGGT TCAGAATATGGCATACCCGGTATTAAAGTCGTCAATTCGGTTTTACG TGCTCATACTGGACTGATAAGGCTGTATTTCGATGCTGTTTATCAGG AACGCAAGTACGGCAGAGGCGATATAAACAAAGAGACCGGTGAGA TACAAGACTAATTAGCAAATGAAATTGGGTGCTCAATTGAGCGCC TTTTTTGTTGTCGGCTAGCCGACTTCTGATACAGGTTTAAGTGTTTT AGCACAACTCCAATTTATTTGGAGTGTAAGTGCGCATTGC |

-continued

| SEQ ID NO | DESCRIPTION | SEQUENCE |
|---|---|---|
| 10 | pLP31-8 check F | GATTAGTCCTCTGCATGATAGGGATAA |
| 11 | pLP31-8 check R | TTTCATGCTCTGACCAACAATTTG |

*L. plantarum* ATIT-031 was isolated from miso. Extraction of plasmids of *L. plantarum* ATIT-031 as well as DNA electrophoresis thereof were performed herein. As shown in FIG. 1, the electrophoresis results indicated that *L. plantarum* ATIT-031 contained multiple plasmids. DNA bands of various molecular weights representing plasmids of *L. plantarum* ATIT-031 were named pLP31-1 to pLP31-8, among which, pLP31-8, the one with the lowest molecular weight, was isolated, cloned, sequenced and analyzed.

Example 4: Construction of Shuttle Vector pBRLP31-8 for *E. coli* and *Lactobacillus*

The shuttle vector in this example was constructed based on the site of replication in *Lactobacillus* plasmid pLP31-8 obtained in Example 1 and *E. coli* plasmid pBR322. This shuttle vector can be applied in both *Lactobacillus* and non-*Lactobacillus* prokaryotic cells.

Figure 2:
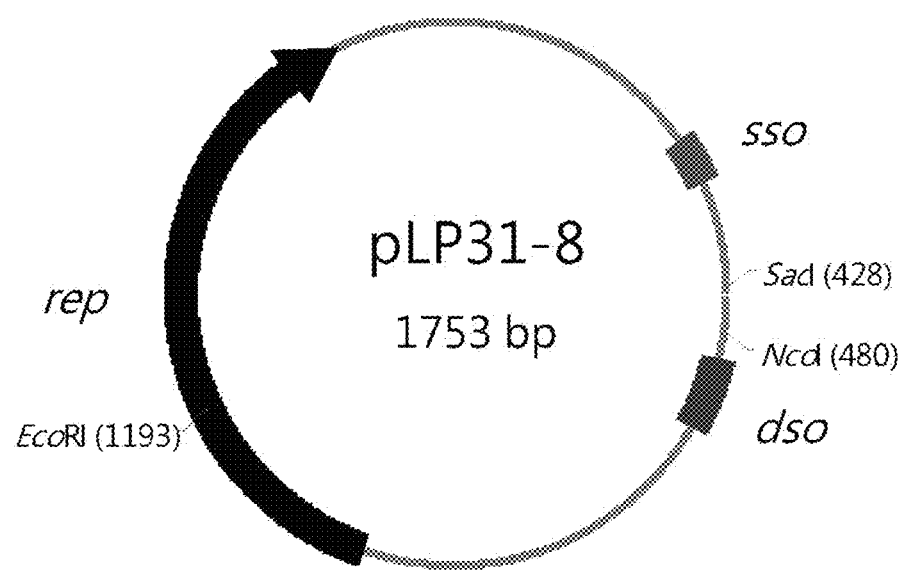
FIG. 2 illustrates the physical map of pLP31-8. Meanings of the abbreviations used therein are as follows: rep: plasmid replicon gene; dso: double-strand origin; and sso: single-strand origin.

Steps of constructing said vector were as follows:
1. Modifications to *Lactobacillus* Region The minimal cryptic plasmid of *L. plantarum* ATIT-031 was 1,753 bp in length, as shown in FIG. 2. According to the sequencing results, this plasmid contained an orf1 region that could encode ORF1 proteins. These ORF1 proteins were predicted to be replication proteins. A single-strand origin (sso) and a double-strand origin (dso) were located at the upstream of the orf1 region (rep). In addition, plasmid pLP31-8 contained an EcoRI cutting site of, which is commonly used for genetic manipulation.

To render future genetic manipulation methods more convenient, mutagenic primers were designed for EcoRI and overlap-extension PCR was used to perform site-directed mutagenesis. Criteria for designing mutagenic primers included centering the mutation in the middle of the primer with a Tm of at least 78° C. The Tm value of the primer was calculated using the following formula provided by Invitrogen:

$$Tm = 81.5 + 0.41(\% \, GC) - 675/N - \% \text{ mismatch}$$

where "% GC" is the percentage of G or C nucleotides in the primer; "N" is the length of the primer; and "% mismatch" is the percentage of mutated bases in the primer.

First, two pairs of mutagenic primers, namely pLP31-8F (as shown in SEQ ID NO: 12)/pLP31-8M2 (as shown in SEQ ID NO: 13) and pLP31-8M1 (as shown in SEQ ID NO: 14)/pLP31-8R (as shown in SEQ ID NO: 15), were designed. Pairs of primers, including pLP31-8F (as shown in SEQ ID NO: 12)/pLP31-8M2 (as shown in SEQ ID NO: 13) and pLP31-8M1 (as shown in SEQ ID NO: 14)/pLP31-8R (as shown in SEQ ID NO: 15), were used separately for amplification of DNA fragments from the plasmid template pLP31-8.

For example, a site of replication in *E. coli* (replicon-pBR322) was amplified from a plasmid template of pET29a (Merck KGaA/Novagen, Germany) using a designed primer pair pBRF/pBRR. This DNA fragment contained an *E. coli* plasmid replicon gene (rep-pBR322) and a gene encoding *E. coli* repressor of primer (cop-pBR322).

The following components were contained in 50 μL PCR reaction mixture: 1× GDP-HiFi PCR Buffer B; 200 μM dATP, dTTP, dGTP and dCTP; 1 μM amplification primer; 100 ng pET29a; and 1 U GDP-HiFi DNA polymerase. A chloramphenicol resistance gene, CM$^r$-pC194, was amplified from a plasmid template of pNW33N (purchased from the Bioresource Collection and Research Center at the Food Industry Research and Development Institute; type culture no. BCRC 41794) using a primer pair CMF/CMR.

The following components were contained in 50 μL PCR reaction mixture: 1× GDP-HiFi PCR Buffer B; 200 μM dATP, dTTP, dGTP and dCTP; 1 μM amplification primer; 100 ng pNW33N; and 1 U GDP-HiFi DNA polymerase. PCR reaction conditions included 96° C. for 2 minutes (1 step); 94° C. for 30 seconds, 55° C. for 30 seconds and 68° C. for 30 seconds (35 cycles); and 68° C. for 5 minutes (1 step). As the above steps completed, agarose gel electro-

| SEQ ID NO | DESCRIPTION | SEQUENCE |
|---|---|---|
| 12 | pLP31-8F | GATATAAGATTTTTTAAAAATAGCAATGAAAAAATCCGA |
| 13 | pLP31-8M2 | CCCCAAACTCCCTTTGGATTCTTTTCCTAACG |
| 14 | pLP31-8M1 | CGTTAGGAAAAGAATCCAAAGGGCTTTGGGG |
| 15 | pLP3I-8R | CAATATGAATTCGCAATGCGCACTTACACTCCA |

The following components were contained in 50 μL PCR reaction mixture: 1× GDP-HiFi PCR Buffer B; 200 μM dATP, dTTP, dGTP and dCTP; 1 μM amplification primer; 100 ng pLP31-8; and 1 U GDP-HiFi DNA polymerase. PCR reaction conditions included 98° C. for 2 minutes (1 step); 94° C. for 30 seconds, 55° C. for 30 seconds and 68° C. for 30 seconds (35 cycles); and 68° C. for 5 minutes (1 step). When the PCR reaction was over, agarose gel electrophoresis was applied to confirm the presence of DNA fragments in the desired size. PCR products were recovered using Gel-M™ gel extraction system kit.

Then, two recovered PCR products served as templates for the DNA amplification and primer pair pLP31-8F (as shown in SEQ ID NO: 12)/pLP31-8R (as shown in SEQ ID NO: 15) was used. PCR reaction conditions included 98° C. for 2 minutes (1 step); 94° C. for 30 seconds, 55° C. for 30 seconds and 68° C. for 1 minute (35 cycles); and 68° C. for 5 minutes (1 step). As the above steps completed, pLP31-8 DNA fragments site-directed mutated were obtained. PCR products were recovered using PCR-M™ Clean Up system kit.

2. Construction of *E. coli* Vector pBRCMMCS

The method for constructing an *E. coli* vector pBRCM-MCS has been described in ROC Patent Application No. 1565799. Based on the method described therein, a person having ordinary skill in the art can understand and construct successfully an *E. coli* vector pBRCMMCS. In short, said vector contains the site of replication of *E. coli* vector pBR322, a chloramphenicol resistance gene and a multiple cloning site.

phoresis was used to confirm the presence of the DNA fragments in the desired size in PCR products.

PCR products were recovered using PCR-M™ Clean Up kit. The replicon-pBR322 and chloramphenicol resistance genes within PCR products were cleaved using SacI and XhoI, and were annealed to each other using T4 DNA ligase. *E. coli* ECOS 9-5 was transformed with the annealed product. Colony PCR was performed using the primer pair CMF/CMR in conjunction with PCR Master Mix II in order to select transformants. PCR reaction conditions included 95° C. for 5 minutes (1 step); 95° C. for 30 seconds, 55° C. for 30 seconds and 72° C. for 1 minute (25 cycles); and 72° C. for 7 minutes (1 step). When the inserted DNAs were confirmed by colony PCR to be present within the recombinant plasmids in the transformants, plasmids in the transformants were extracted and sequenced. Plasmids having the correct sequence were named pBRCM.

Synthesis of multiple cloning sites was performed using overlap-extension polymerase chain reaction (OEPCR); wherein restriction enzyme cutting sites included BglII, EcoRI, SpeI, NdeI, BamHI, XmaI, PstI, SalI, HindIII, XhoI and XbaI were designed. During a PCR reaction, primers were annealed to the template, thereby allowing the polymerase to synthesize a full-length DNA by extending the primers in the 5' to 3' direction, based on the 3' to 5' primers acted as templates.

DNA fragments were amplified by amplification primers based on the full-length DNA as a template. The following components were contained in 50 μL PCR reaction mixture: 1× GDP-HiFi PCR Buffer B; 200 μM dATP, dTTP, dGTP and dCTP; 1 μM primer; and 1 U GDP-HiFi DNA polymerase. PCR reaction conditions included 96° C. for 2 minutes (1 step); 94° C. for 30 seconds, 55° C. for 30 seconds and 68° C. for 30 seconds (35 cycles); and 68° C. for 5 minutes (1 step). As the above steps completed, agarose gel electrophoresis was used to confirm the presence of the DNA fragments in the desired size in PCR products.

PCR products were recovered using PCR-M™ Clean Up kit. The synthesized multiple cloning sites were cleaved using BglII and XhoI, and were annealed to the pBRCM cleaved by the same restriction enzyme using T4 DNA ligase. E. coli ECOS 9-5 was transformed with the annealed product. Colony PCR was performed using the primer pair MCSF/MCSR in conjunction with PCR Master Mix II in order to select transformants. PCR reaction conditions included 95° C. for 5 minutes (1 step); 95° C. for 30 seconds, 55° C. for 30 seconds and 72° C. for 30 seconds (25 cycles); and 72° C. for 7 minutes (1 step). When the inserted DNAs were confirmed by colony PCR to be present within the recombinant plasmids in the transformants, plasmids in the transformants were extracted and sequenced. Plasmids having the correct sequence were named pBRCMMCS.

3. Construction of Shuttle Vector pBRLP31-8

Figure 3:
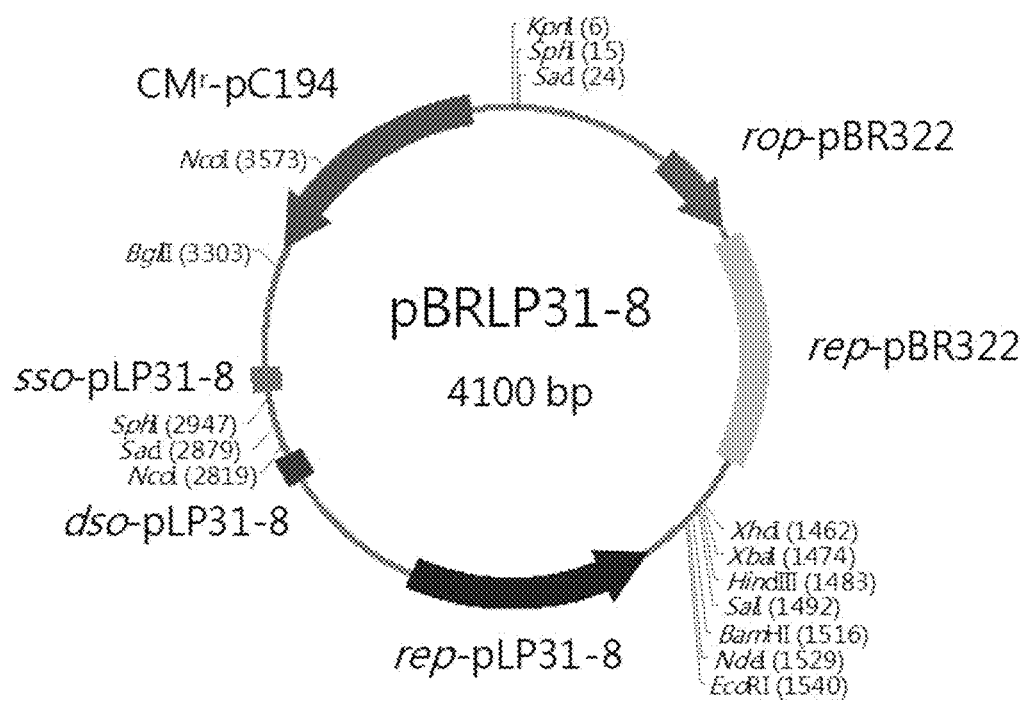
FIG. 3 illustrates the physical map of pBRLP31-8. Meanings of the abbreviations used therein are as follows: rop-pBR322: gene encoding repressor of primer of pBR322: rep-pBR322: replicon gene of pBR322; rep-pLP31-8: plasmid replicon gene of pLP31-8; dso-pLP31-8: double-strand origin of pLP31-8; sso-pLP31-8: single-strand origin of pLP31-8; and Cm$^r$-pC194: chloramphenicol resistance gene of pC194.

In short, PCR products obtained from Step 1 that originated from a *Lactobacillus* region were cleaved by BglII and EcoRI, and were annealed to the pBRCMMCS (i.e. *E. coli* region) cleaved by the same restriction enzyme by T4 DNA ligase. *E. coli* ECOS 9-5 was transformed with the annealed product. Colony PCR was performed using the primer pair pLP31-8F (as shown in SEQ ID NO: 12)/pLP31-8R (as shown in SEQ ID NO: 15) in conjunction with Dream taq DNA polymerase in order to select transformants. PCR reaction conditions included 95° C. for 5 minutes (1 step); 95° C. for 30 seconds, 55° C. for 30 seconds and 72° C. for 2 minutes (25 cycles); and 72° C. for 7 minutes (1 step). When the inserted DNAs were confirmed by colony PCR to be present within the recombinant plasmids in the transformants, plasmids in the transformants were extracted and sequenced. Plasmids having the correct sequence were named pBRLP31-8.

pBRLP31-8 contained the site of replication of *E. coli* vector pBR322, a chloramphenicol resistance gene, a multiple cloning site, and site-directed mutated pLP31-8. See FIG. 3 for the physical map of plasmid pBRLP31-8, and SEQ ID NO: 2 for its sequence.

| SEQ ID NO | DESCRIPTION | SEQUENCE |
|---|---|---|
| 2 | Complete sequence of pBREP31-8 | GGTACCAAAGCATGCAATGAGCTCAGTAACCCGTATCGTGAG<br>CATCCTCTCTCGTTTCATCGGTATCATTACCCCCATGAACAGA<br>AATCCCCCTTACACGGAGGCATCAGTGACCAAACAGGAAAA<br>AACCGCCCTTAACATGGCCCGCTTTATCAGAAGCCAGACATT<br>AACGCTTCTGGAGAAACTCAACGAGCTGGACGCGGATGAAC<br>AGGCAGACATCTGTGAATCGCTTCACGACCACGCTGATGAG<br>CTTTACCGCAGCTGCCTCGCGCGTTTCGGTGATGACGGTGAA<br>AACCTCTGACACATGCAGCTCCCGGAGACGGTCACAGCTTG<br>TCTGTAAGCGGATGCCGGGAGCAGACAAGCCCGTCAGGGCG<br>CGTCAGCGGGTGTTGGCGGGTGTCGGGGCGCAGCCATGACC<br>CAGTCACGTAGCGATAGCGGAGTGTATACTGGCTTAACTATG<br>CGGCATCAGAGCAGATTGTACTGAGAGTGCACCATTGCGGT<br>GTGAAATACCGCACAGATGCGTAAGGAGAAAATACCGCATC<br>AGGCGCTCTTCCGCTTCCTCGCTCACTGACTCGCTGCGCTCG<br>GTCGTTCGGCTGCGGCGAGCGGTATCAGCTCACTCAAAGGC<br>GGTAATACGGTTATCCACAGAATCAGGGGATAACGCAGGAA<br>AGAACATGTGAGCAAAAGGCCAGCAAAAGGCCAGGAACCG<br>TAAAAAGGCCGCGTTGCTGGCGTTTTTCCATAGGCTCCGCCC<br>CCCTGACGAGCATCACAAAAATCGACGCTCAAGTCAGAGGT<br>GGCGAAACCCGACAGGACTATAAAGATACCAGGCGTTTCCC<br>CCTGGAAGCTCCCTCGTGCGCTCTCCTGTTCCGACCCTGCCG<br>CTTACCGGATACCTGTCCGCCTTTCTCCCTTCGGGAAGCGTG<br>GCGCTTTCTCATAGCTCACGCTGTAGGTATCTCAGTTCGGTGT<br>AGGTCGTTCGCTCCAAGCTGGGCTGTGTGCACGAACCCCCC<br>GTTCAGCCCGACCGCTGCGCCTTATCCGGTAACTATCGTCTT<br>GAGTCCAACCCGGTAAGACACGACTTATCGCCACTGGCAGC<br>AGCCACTGGTAACAGGATTAGCAGAGCGAGGTATGTAGGCG<br>GTGCTACAGAGTTCTTGAAGTGGTGGCCTAACTACGGCTACA<br>CTAGAAGGACAGTATTTGGTATCTGCGCTCTGCTGAAGCCAG<br>TTACCTTCGGAAAAAGAGTTGGTAGCTCTTGATCCGGCAAAC<br>AAACCACCGCTGGTAGCGGTGGTTTTTTTGTTTGCAAGCAGC<br>AGATTACGCGCAGAAAAAAAGGATCTCAAGAAGATCCTTTG<br>ATCTTTTCTACGGGGTCTGACGCTCAGTGGAACGAAAACTCA<br>CGTTAAGGGATTTTGGTCATGAACAATAAAACTGTCTGCTTA<br>CATAAACAGTAATACAAGGGGTGTTATGAGCCATATCAACGG<br>GAAACGCTCGAGTACGTATCTAGAGCAAAGCTTATCGTCGAC<br>ATGCATCTGCAGCCCGGGGGATCCTCGCGACATATGACTAGT<br>GAATTCGCAATGCGCACTTACACTCCAAATAAATTGGAGTTG<br>TGCTAAAACACTTAAACCTGTATCAGAAGTCGGCTAGCCGAC<br>AACAAAAAAGGCGCTCAATTGAGCACCCAATTTTCATTTGCT<br>AATTAGTCTTGTATCTCACCGGTCTCTTTGTTTATATCGCCTCT<br>GCCGTACTTGCGTTCCTGATAAACAGCATCGAAATACAGCCT<br>TATCAGTCCAGTATGAGCACGTAAAACCGAATTGACGACTTT<br>AATACCGGGTATGCCATATTCTGAACCATGAGCTTTTAAAAA<br>GCGTCTCAGTTCACGCATATTTGCCAAATTATGGTCATCAATC<br>AAATCACAAACATCATTCAGCATGTCGTCTTTGTCTTCAACAT<br>CAAGCGTAATATAGCGATCAATATCAAAATTGTTCAGCAAAGT<br>AATGTCGTGCTTGCTGTACTTGTGCTTATTTTTAGCAATAGCG<br>TCTTTAGATTCATGTGTCAGATACAAATACATATTTTTCATGCT<br>CTGAGCAACAATTTGCACTTTAGAAACGCTTCTAGGCCCCAA |

-continued

| SEQ ID NO | DESCRIPTION | SEQUENCE |
|---|---|---|
| | | AGCCCTTTGGATTCTTTTCCTAACGCTATCCGTCGTAACAGGA |
| | | TTTTTTGCCACATAAACAACATGATAATGAGCTTTCTTGTACG |
| | | TCTGCCCTTCAACATTGCTCTTATCCCTATCATGCAGAGGACT |
| | | AATCGCAATAGGAACGCCCATCAGTTCCAAGCGTTGATTCCA |
| | | ATCATTTGGAATACTTTCCGGATATAGCAAAAAAGTGAAGTA |
| | | CCTTGCCTTGTCTTTAGCCATAATGTTAAAATCGCCTTATCAG |
| | | AATAAGCAACAATCGAGCGAACTTTTCAGCGGGTACGCTCTT |
| | | TTTTTGTGCTCATTTCTGCCCTTCCTTGTATTTTTCTAGTGCAA |
| | | CTGTAATCAATGCAGATTTAGATAAACCTTTGTTTTTCGCAGT |
| | | CTCCGACAAATATTCAAGAACTTGACTCGATAACGTAATCGT |
| | | CAATCTCTTTTTACTTTCCAAAATTTCTAACCTCCTTCAAATAT |
| | | TCACTAAAGAAAAAGTAGCATAATTACGTATTTAATGCAACA |
| | | AAATACGTATTAAATTCAAAAAAATCACCAAAATGTCGCCAA |
| | | AATGTCGCTCAATAATAAAGTGGACTAATCCCTTGGGAGAGT |
| | | AGACCTGAAGCCACCTAAAATTCAGTTTTGGCACTCGGCACT |
| | | TAAAGGGGGGGTCGTAGTACGGTCGCAAAATTCGCTCCCTC |
| | | GCCCCCCCTGATTTTCAAATTTCTATCCCACACGAATAAAACC |
| | | ATGGGCGCTGCCCAAACCCGCAAGCTGTGTCAGCTTGACCC |
| | | CATAAATGAGCGGGAGCTCCCGCTCAAACTCACCCTGCACTC |
| | | GCCGTGAGGCAGGCAAAAAAAGCAGGTGTGCTTTTCTTTGC |
| | | ATGCGCAAAAGTGTCTTGGTCTAGTGAGTCTGTCAACTCCTT |
| | | AAAGCCTCCTAGAACGGCTAAAAGCCGTTCTACGTCGATTTA |
| | | CCGTTGACGGACAGTAAATTATACGGTTAACAGCTAAAATGG |
| | | CTTAGAGAGCAAATTAGGGGCATTTAAAGCCAATCTTTAAAG |
| | | CCAATAAAGTCCGAAgGAGTTGGCGACTGGACTTTATTGGCT |
| | | TTAAAGATTCCAACTGACGCAAGTCAGTTTTGTTTGAGCAAA |
| | | GCGAAATCTGATACAGTTTTAATGGGTTTAGCACAGCGTCAT |
| | | CTTTGATGACGTGTAAGTGTACCTTTGACATTTTCTTCGGATT |
| | | TTTTCATTGCTATTTTTAAAAGATCTTAGTGACATTAGAAAAC |
| | | CGACTGTAAAAAGTACAGTCGGCATTATCTCATATTATAAAAG |
| | | CCAGTCATTAGGCCTATCTGACAATTCCTGAATAGAGTTCATA |
| | | AACAATCCTGCATGATAACCATCACAAACAGAATGATGTACC |
| | | TGTAAAGATAGCGGTAAATATATTGAATTACCTTTATTAATGAA |
| | | TTTTCCTGCTGTAATAATGGGTAGAAGGTAATTACTATTATTAT |
| | | TGATATTTAAGTTAAACCCAGTAAATGAAGTCCATGGAATAAT |
| | | AGAAAGAGAAAAAGCATTTTCAGGTATAGGTGTTTTGGGAA |
| | | ACAATTTCCCCGAACCATTATATTTCTTCTACATCAGAAAGGTA |
| | | TAAATCATAAAACTCTTTGAAGTCATTCTTTACAGGAGTCCA |
| | | AATACCAGAGAATGTTTTAGATACACCATCAAAAATTGTATAA |
| | | AGTGGCTCTAACTTATCCCAATAACCTAACTCTCCGTCGCTAT |
| | | TGTAACCAGTTCTAAAAGCTGTATTTGAGTTTATCACCCTTGT |
| | | CACTAAGAAAATAAATGCAGGGTAAAATTTATATCCTTCTTGT |
| | | TTTATGTTTCGGTATAAAACACTAATATCAATTTCTGTGGTTAT |
| | | ACTAAAAGTCGTTTGTTGGTTCAAATAATGATTAAATATCTCT |
| | | TTTCTCTTCCAATTGTCTAAATCAATTTTATTAAACTTTCATTTG |
| | | ATATGCCTCCTAAATTTTTATCTAAAGTGAATTTAGGAGGCTT |
| | | ACTTGTCTGCTTTCTTCATTAGAATCAATCCTTTTTTAAAAGT |
| | | CAATCC |

Example 5: Analysis of Shuttle Vector pBRLP31-8

In this example, the shuttle vector pBRLP31-8 obtained from Example 4 was transformed into *L. plantarum*, *L. rhamnosus*, *W. cibaria* and *B. subtilis*. The characteristics of pBRLP31-8 therein were observed and the copy number of pBRLP31-8 in each of said strains was examined separately.

1. Transformation of *L. plantarum* and *L. rhamnosus*, and Analysis of Transformants Thereof A 30 mL MRS medium was inoculated with a selected single colony and incubated at 30° C. After overnight incubation, an appropriate amount of broth was transferred to a 200 mL MRS medium containing 3% glycine, an initial $OD_{600}$ was adjusted to 0.1, and the incubation at 30° C. was continued. After 5 hours of incubation, pellet was collected by centrifugation (12,000×g, 10 minutes, 4° C.), and 200 mL wash buffer (5 mM sodium phosphate, 1 mM $MgCl_2$, pH 7.4) was added to the medium to properly suspend the pellet. The resulting mixture was centrifuged (12,000×g, 10 minutes, 4° C.), the supernatant was properly discarded and 1 mL electroporation buffer (0.9 M sucrose, 3 mM $MgCl_2$) was added in order to properly suspend the pellet. The resulting mixture was centrifuged (12,000×g, 10 minutes, 4° C.), the supernatant was properly discarded, and an appropriate amount of electroporation buffer was added in order to properly suspend the pellet. The resulting mixture was aliquoted into microcentrifuge tubes (100 μL per tube), and the tubes were quick-frozen in liquid nitrogen and stored at −70° C. for future use. During transformation of DNA, 1 μg plasmid DNA was added into 100 μL electrocompetent cells and the resulting mixture was put into pre-cooled electrode tubes. After being immersed in a cooling bath for 5 minutes, the electrode tubes were removed and electrotransformed at a field strength of 8.75 kV/cm with a 25 μF capacitor. The electrotransformed cells were added to a 1 mL MRS medium and incubated at 30° C. for 2 hours. An appropriate amount of broth was spread over the surface of an MRS solid culture plate containing 5 μg/mL chloramphenicol, and the culture plate was cultured at 30° C. under anaerobic conditions for 48 hours before being observed. Plasmids of *Lactobacillus* transformants were extracted using Plasmid Miniprep Purification Kit II. The plasmids extracted from transformants were further cleaved by BglII and BglII/EcoRI, and the cleavage products of plasmid DNA were examined by agarose gel electrophoresis. As shown in FIGS. 4(A) and 4(B), arrows indicate bands obtained from the shuttle vector pBRLP31-8, either cleaved by restriction enzymes or uncleaved, which was transformed to L. plantarum and L. rhamnosus. Sizes of the plasmids corresponded to expected values.

2. Transformation of W. cibaria, and Analysis of Transformants Thereof

A 30 mL MRS medium was inoculated with a selected single colony and incubated at 30° C. After overnight incubation, a 200 mL MRS medium containing 1% glycine was inoculated with 16 mL broth, and the incubation at 30° C. was continued. After 3.5 hours of incubation, pellet was collected by centrifugation (12,000×g, 10 minutes, 4° C.), and 64 mL sterile TSLD buffer (10 mM Tris, 0.6 M sucrose, 0.1 M lithium acetate, 0.01 M DTT, pH 7.5) was added to the medium to suspend the pellet. The resulting mixture was incubated at 37° C. for 20 minutes and centrifuged (12,000×g, 10 minutes, 4° C.). After centrifugation, the supernatant was properly discarded and 200 mL pre-cooled, sterile electroporation buffer was added in order to properly suspend the pellet. The resulting mixture was centrifuged (12,000×g, 10 minutes, 4° C.), the supernatant was properly discarded and the step of mixing with electroporation buffer was repeated three times. An appropriate amount of electroporation buffer was added in order to properly suspend the pellet. The resulting mixture was aliquoted into microcentrifuge tubes (100 μL per tube), and the tubes were quick-frozen in liquid nitrogen and stored at −70° C. for future use. During transformation of DNA, 1 μg plasmid DNA was added into 100 μL electrocompetent cells and the resulting mixture was put into pre-cooled electrode tubes. After being immersed in a cooling bath for 5 minutes, the electrode tubes were removed and electrotransformed at a field strength of 8.75 kV/cm with a 25 μF capacitor. The electrotransformed cells were added to a 1 mL MRS medium and incubated at 30° C. for 2 hours. An appropriate amount of broth was spread over the surface of an MRS solid culture plate containing 5 μg/mL chloramphenicol, and was cultured at 30° C. under anaerobic conditions for 48 hours before being observed. Plasmids extracted from the transformants were further cleaved by BglII and BglII/EcoRI, and the cleavage products of plasmid DNA were examined by agarose gel electrophoresis. As shown in FIG. 4(C), arrows indicate bands obtained from the shuttle vector pBRLP31-8, either cleaved by restriction enzymes or uncleaved, which was transformed to W. cibaria. Sizes of the plasmids corresponded to expected values.

3. Transformation of B. subtilis, and Analysis of Transformants Thereof

A 50 mL LB medium was inoculated with a selected single colony and incubated on a shaker at 180 rpm at 37° C. After overnight incubation, a 400 mL LB medium containing 0.5% glycine was inoculated with 40 mL broth, an initial $OD_{600}$ was adjusted to 0.1, and the incubation at 37° C. was continued. After 5 hours of incubation, pellet was collected by centrifugation (12,000×g, 10 minutes, 4° C.), and 200 mL sterile water was added to the medium to properly suspend the pellet. The resulting mixture was centrifuged (12,000×g, 10 minutes, 4° C.), the supernatant was properly discarded and 2 mL pre-cooled, sterile SHMPYT buffer [0.25 M sucrose, 1 mM HEPES, 1 mM $MgCl_2$, 20% (v/v) polyethylene glycol 6000 (PEG6000), 0.125% yeast extract, 0.25 tryptone] was added in order to properly suspend the pellet. The resulting mixture was centrifuged (12,000×g, 10 minutes, 4° C.), the supernatant was properly discarded, and an appropriate amount of SHMPYT buffer was added in order to properly suspend the pellet. The resulting mixture was aliquoted into microcentrifuge tubes (100 μL, per tube), and the tubes were quick-frozen in liquid nitrogen and stored at −70° C. for future use. During transformation of DNA, 1 μg plasmid DNA was added into 100 μL electrocompetent cells and the resulting mixture was put into pre-cooled electrode tubes. After being immersed in a cooling bath for 5 minutes, the electrode tubes were removed and electrotransformed at a field strength of 10 kV/cm with a 25 μF capacitor. The electrotransformed cells were added to a 1 mL Select APS™ Super Broth medium and incubated on a shaker at 80 rpm at 37° C. for 2 hours. An appropriate amount of broth was spread over the surface of an LB solid culture plate containing 5 μg/mL chloramphenicol, and was cultured at 37° C. for 24-48 hours before being observed. Plasmids extracted from transformants were further cleaved by BglII and BglII/EcoRI and the cleavage products of plasmid DNA were examined by agarose gel electrophoresis. As shown in FIG. 4(D), arrows indicate bands obtained from the shuttle vector pBRLP31-8, either cleaved by restriction enzymes or uncleaved, which was transformed to B. subtilis. Sizes of the plasmids corresponded to expected values.

4. Examination of Relative Copy Number of pBRLP31-8 in L. plantarum, L. rhamnosus, W. cibaria, and B. subtilis Using Real-Time Polymerase Chain Reaction Real-time PCR primer pairs were designed for tuf genes of L. plantarum and L. rhamnosus, pepX gene of W. cibaria, amyE gene of B. subtilis, and DNA fragments of pLP31-8. The primer pair designed for tuf gene of L. plantarum was LPTufF (SEQ ID NO: 16)/LPTufR (SEQ ID NO: 17); the primer pair designed for tuf gene of L. rhamnosus was LGGTufF (SEQ ID NO: 18)/LGGTufR (SEQ ID NO: 19); the primer pair designed for pepX of W. cibaria was PepXF (SEQ ID NO: 20)/PepXR (SEQ ID NO: 21); the primer pair designed for amyE of B. subtilis was AmyF (SEQ ID NO: 22)/AmyR (SEQ ID NO: 23); and the primer pair designed for the DNA fragments of pLP31-8 was pLp31-8RTF (SEQ ID NO: 24)/pLp31-8RTR (SEQ ID NO: 25).

| SEQ ID NO | DESCRIPTION | SEQUENCE |
| --- | --- | --- |
| 16 | LPTufT | TTCCTGTTATCCGTGGTTCA |
| 17 | LPTufR | AACAGGCATCAAGAAAGGCT |
| 18 | LGGTufR | ACCTTGGATCTTGGTGAAGC |
| 19 | LGGTufR | TCAACTTGGTCACGGTTGAT |
| 20 | PepXF | GGGACAAACATGCGTTACT |

-continued

| SEQ ID NO | DESCRIPTION | SEQUENCE |
|---|---|---|
| 21 | PepXR | TTCACGACCGATTAGAACCA |
| 22 | AmyF | TTCCTGTTATCCGTGGTTCA |
| 23 | AmyR | AACAGGCATCAAGAAAGGCT |
| 24 | pLp31-8RTF | GCGAGTGCAGGGTGAGTTTG |
| 25 | pLp31-8RTR | GGGTCGTAGTACGGTCGCAA |

The whole DNAs of different strains were extracted using DNeasy Blood & Tissue Kit. Reagents were prepared with Faststart Universal SYBR Green Master (ROX). 10 ng, 1 ng, 0.1 ng, and 0.01 ng of the whole DNAs were used separately in 25 μL reaction volume. Real-time PCR was performed using ViiA™ 7 Real Time PCR System (Life Technologies, USA). A standard curve was created by plotting the threshold cycle (Ct) obtained from the reactions against $\log_{10}$ of the amount of the whole DNAs used.

The slope of each standard curve was determined, and PCR efficiency (E) was determined using the formula: $E=10^{-1/slope}$; wherein the E value of genomic gene was defined as Ec, and E value of pLP31-8 DNA fragments was defined as Ep. The mean Ct values of reactions of genomic gene as well as pLP31-8 DNA fragments were calculated separately; wherein the mean Ct value of genomic gene reactions was defined to as Ctc, and the mean Ct value of reactions of pLP31-8 DNA fragments was defined as Ctp. The formula for determining a relative copy number of a plasmid is $(EC)^{Ctc}/(EP)^{Ctp}$.

5. Results of *E. coli/Lactobacillus* Shuttle Vector pBRLP31-8 Transformation

Figure 4:
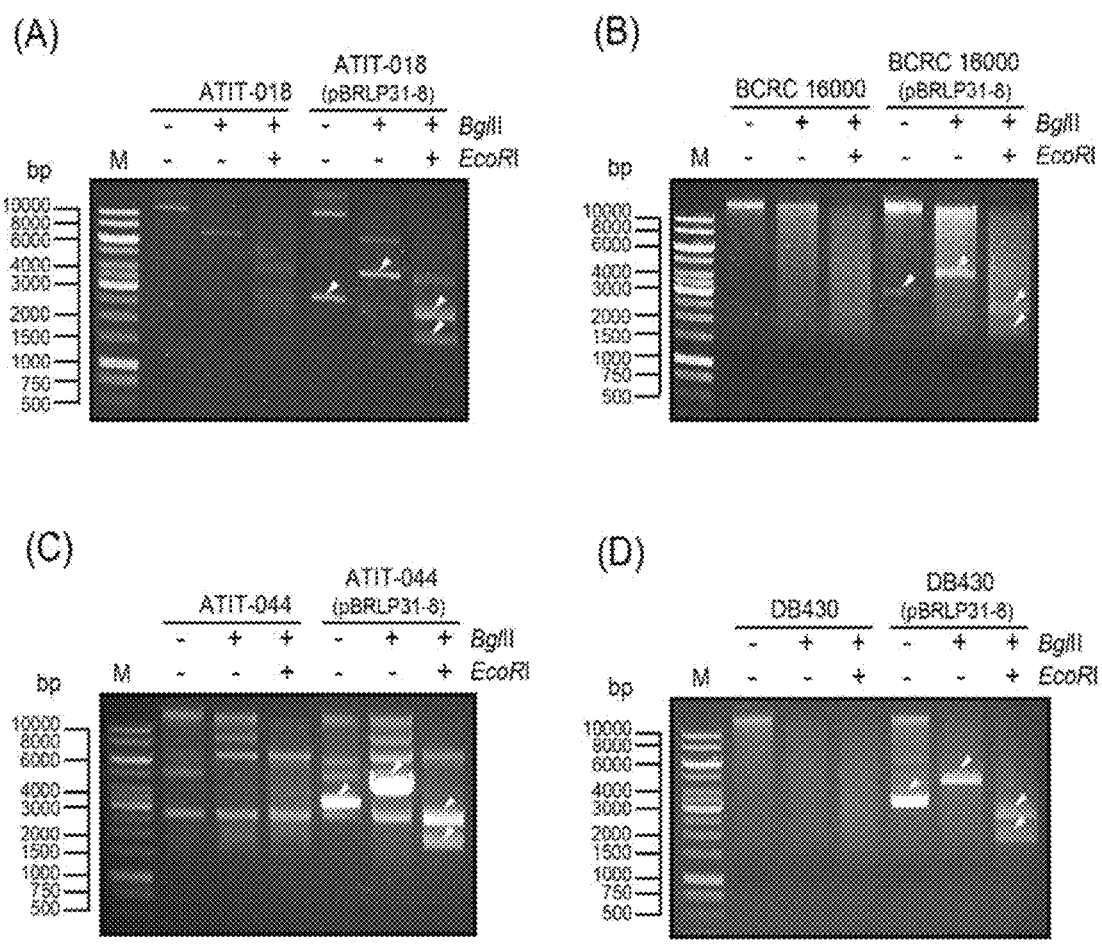
FIG. 4 illustrates the confirmation of the presence of plasmid pBRLP31-8 in transformants of *L. plantarum* ATIT-018, *L. rhamnosus* BCRC 16000, *W. cibaria* ATIT-044 and *B. subtilis* DB430. (A) Gel electrophoresis results performed on the plasmids that were extracted from *L. plantarum* ATIT-018 strains containing or not containing plasmid pBRLP31-8 and cleaved by restriction enzymes. (B) Gel electrophoresis results performed on the plasmids that were extracted from *L. rhamnosus* BCRC 16000 strains containing or not containing plasmid pBRLP31-8 and cleaved by restriction enzymes. (C) Gel electrophoresis results performed on the plasmids that were extracted from *W. cibaria* ATIT-044 strains containing or not containing plasmid pBRLP31-8 and cleaved by restriction enzymes. (D) Gel electrophoresis results performed on the plasmids that were extracted from *B. subtilis* DB430 strains containing or not containing plasmid pBRLP31-8 and cleaved by restriction enzymes.

As described in the previous example, pBRLP31-8 was transformed into *L. plantarum* ATIT-018, *L. rhamnosus* BCRC 16000, *W. cibaria* ATIT-044, and *B. subtilis* DB430 by electroporation. Results showed that the transformants were able to form colonies on solid selective culture plate containing antibiotic, meaning that they were resistant to the antibiotic (not shown in the figures). As shown in FIG. 4, the presence of pBRLP31-8 in all transformants was confirmed after plasmids were extracted from transformants and analyzed by restriction enzyme digestion. It is apparent from the above results that pBRLP31-8 can be used as a novel shuttle vector in genetic engineering studies on various types of host cells, such as *E. coli*, *L. plantarum*, *L. rhamnosus*, *W. cibaria* and *B. subtilis*.

6. Relative Copy Numbers of pBRLP31-8 in Different Hosts

Relative copy numbers of pBRLP31-8 in different hosts were determined using real-time quantitative polymerase chain reaction. Results showed that the copy numbers of pBRLP31-8 in *L. plantarum* ATIT-018, *L. rhamnosus* BCRC 16000, *W. cibaria* ATIT-044 and *B. subtilis* DB430 were 1, 5, 18 and 34, respectively (as shown in Table 1), suggesting that pBRLP31-8 could replicate effectively at least in *L. plantarum*, *L. rhamnosus*, *W. cibaria* and *B. subtilis*.

TABLE 1

Determining copy numbers of pBRLP31-8 in different hosts using real-time quantitative polymerase chain reaction

| Host | Target | Ct value for different amounts of DNA | | | | E | Mean Ct | Copy number of plasmid |
|---|---|---|---|---|---|---|---|---|
| | | 10 ng | 1 ng | 0.1 ng | 0.01 ng | | | |
| *L. plantarum* | tuf | 17.44 | 20.91 | 24.47 | 27.93 | 1.93 | 22.69 | 1 |
| | pLP31-8 | 17.06 | 20.54 | 24.07 | 27.58 | 1.93 | 22.31 | |
| *L. rhamnosus* | tuf | 22.45 | 25.92 | 29.21 | 32.50 | 1.99 | 27.52 | 5 |
| | pLP31-8 | 20.87 | 24.26 | 27.71 | 31.20 | 1.95 | 26.01 | |
| *W. cibaria* | pepX | 17.71 | 21.17 | 24.65 | 27.97 | 1.96 | 22.88 | 18 |
| | pLP31-8 | 13.32 | 16.85 | 20.24 | 23.59 | 1.96 | 18.50 | |
| *B. subtilis* | amyE | 16.71 | 20.11 | 23.50 | 26.97 | 1.96 | 21.82 | 34 |
| | pLP31-8 | 11.49 | 14.99 | 18.30 | 21.80 | 1.96 | 16.65 | |

E: PCR efficiency

Example 6: Method and Kit for Producing Proteins

In one example, nucleic acid sequences of interested gene could be expressed in an appropriate host cell to product corresponding proteins. In short, a prokaryotic host cell was transferred into a medium and cultured under suitable conditions so as to express said proteins; and said proteins were recovered from the host cell or from the broth of the host cell. Steps of said method as well as said reaction conditions are known to a person having ordinary skill in the art and can be found in detail in Sambrook et al., Molecular Cloning: A Laboratory Manual (Cold Spring Harbor Laboratory, 1989). In some examples, the method for producing proteins described herein further comprises constructing an expression vector that contains a target gene using said shuttle vector, and transforming said expression vector into a host cell so that the host cell is able to express the target gene.

In some examples, a kit for expressing exogenous genes may be used to transform a host cell and to produce corresponding proteins in the host cell; wherein said kit comprises said shuttle vector.

Based on the disclosure herein, all disclosed and claimed shuttle vectors, the host cell and kit containing all the shuttle vectors, as well as the method for producing proteins using said host cell can be obtained and applied without undue experimentation. The technical features of the present application that have been disclosed via above preferred examples are not to be taken in a limiting sense for the present invention. Any changes or modifications made thereto without departing from the spirit of the invention shall all be included in the protection scope of the invention.

What is claimed is:

1. A shuttle vector, comprising:
   (a) an *E. coli* plasmid replicon gene comprising SEQ ID NO: 3; and
   (b) a *Lactobacillus* plasmid replicon gene comprising SEQ ID NO: 4.

2. The shuttle vector of claim 1, wherein the shuttle vector comprises SEQ ID NO: 2.

3. The shuttle vector of claim 1, further comprising a single-strand origin and a double-strand origin.

4. The shuttle vector of claim 1, further comprising a multiple cloning site.

5. The shuttle vector of claim 4, further comprising an expression element upstream of the multiple cloning site.

6. The shuttle vector of claim 1, further comprising a selectable marker.

7. The shuttle vector of claim 6, wherein the selectable marker is selected from the group consisting of an antibiotic resistance marker gene, a non-antibiotic resistance marker gene, and a combination thereof.

8. The shuttle vector of claim 7, wherein the selectable marker is a chloramphenicol resistance gene.

9. The shuttle vector of claim 1, wherein the shuttle vector can replicate in a prokaryotic host cell selected from the group consisting of *Escherichia coli*, *Lactobacillus plantarum*, *Lactobacillus rhamnosus*, *Weissella cibaria*, *Bacillus subtilis* and a combination thereof.

10. The shuttle vector of claim 1, further comprising a gene encoding *E. coli* repressor of primer comprising SEQ ID NO: 5.

11. A prokaryotic host cell, comprising the shuttle vector of claim 1.

12. The prokaryotic host cell of claim 11, wherein the prokaryotic host cell is selected from the group consisting of *Escherichia coli*, *Lactobacillus plantarum*, *Lactobacillus rhamnosus*, *Weissella cibaria*, *Bacillus subtilis*, and a combination thereof.

13. A method for producing proteins, wherein the method comprises:
   constructing an expression vector using the shuttle vector of claim 1;
   culturing a cell comprising the expression vector in a culture medium to express the proteins; and
   recovering the proteins from the cell or from the culture medium of the cell.

14. The method of claim 13, further comprising transforming the cell with the expression vector.

15. A shuttle vector, comprising:
   a *Lactobacillus* region comprising SEQ ID NO: 6; wherein the *Lactobacillus* region comprises:
   a single-strand origin;
   a double-strand origin; and
   a *Lactobacillus* replicon gene; and
   an *E. coli* region comprising SEQ ID NO: 7; wherein the *E. coli* region comprises:
   an *E. coli* plasmid replicon gene; and
   a gene encoding *E. coli* repressor of primer.

16. The shuttle vector of claim 15, wherein the *E. coli* plasmid replicon gene is rep of *E. coli* plasmid pBR322, and the gene encoding *E. coli* repressor of primer is rop of *E. coli* plasmid pBR322.

17. The shuttle vector of claim 15, further comprising a selectable marker, wherein the selectable marker is selected from the group consisting of an antibiotic resistance marker gene, a non-antibiotic resistance marker gene, and a combination thereof.

18. The shuttle vector of claim 17, wherein the selectable marker is a chloramphenicol resistance gene.

19. The shuttle vector of claim 15, further comprising a multiple cloning site.

20. The shuttle vector of claim 19, further comprising an expression element upstream of the multiple cloning site.

21. A kit for expressing exogenous genes, comprising: a shuttle vector comprising:
   (a)
   an *E. coli* plasmid replicon gene comprising SEQ ID NO: 3; and
   a *Lactobacillus* plasmid replicon gene comprising SEQ ID NO: 4; or
   (b)
   a *Lactobacillus* region comprising SEQ ID NO: 6, wherein the *Lactobacillus* region comprises:
   a single-strand origin;
   a double-strand origin; and
   a *Lactobacillus* replicon gene; and
   an *E. coli* region comprising SEQ ID NO: 7, wherein the *E. coli* region comprises:
   an *E. coli* plasmid replicon gene; and
   a gene encoding *E. coli* repressor of primer.

22. A method for producing proteins, wherein the method comprises:
   constructing an expression vector using the shuttle vector of claim 15;
   culturing a cell comprising the expression vector in a culture medium to express the proteins; and
   recovering the proteins from the cell or from the culture medium of the cell.

* * * * *